(12) United States Patent
Lehmann et al.

(10) Patent No.: US 8,551,732 B2
(45) Date of Patent: Oct. 8, 2013

(54) INCREASED PRODUCTION OF A TARGET PRODUCT VIA STABILIZATION OF MRNA

(75) Inventors: Martin Lehmann, Grenzach-Wyhlen (DE); Zoltan Pragai, Ranizwiller (FR); Michéle Schaber, Basel (CH)

(73) Assignee: DSM IP Assets B.V., Heerlen (NL)

( * ) Notice: Subject to any disclaimer, the term of this patent is extended or adjusted under 35 U.S.C. 154(b) by 673 days.

(21) Appl. No.: 12/601,614

(22) PCT Filed: Jun. 9, 2008

(86) PCT No.: PCT/EP2008/004583
§ 371 (c)(1),
(2), (4) Date: Feb. 3, 2010

(87) PCT Pub. No.: WO2008/148575
PCT Pub. Date: Dec. 11, 2008

(65) Prior Publication Data
US 2010/0173356 A1    Jul. 8, 2010

(30) Foreign Application Priority Data

Jun. 7, 2007  (EP) .................................... 07011200
Jun. 11, 2007 (EP) .................................... 07011415
Jun. 14, 2007 (EP) .................................... 07011681

(51) Int. Cl.
| C12P 25/00 | (2006.01) |
| C12P 17/16 | (2006.01) |
| C12P 13/04 | (2006.01) |
| C12P 17/12 | (2006.01) |
| C12P 17/18 | (2006.01) |
| C12N 15/74 | (2006.01) |
| C12N 15/75 | (2006.01) |

(52) U.S. Cl.
USPC ............. 435/66; 435/119; 435/106; 435/122; 435/471; 435/252.31

(58) Field of Classification Search
USPC ............... 435/66, 119, 106, 122, 252.31, 471
See application file for complete search history.

(56) References Cited

U.S. PATENT DOCUMENTS 5,017,477 A    5/1991  Sloma et al.
2008/0299662 A1   12/2008  Ferrandez et al.

FOREIGN PATENT DOCUMENTS

EP    0 227 260    7/1987
WO    2007/065602   6/2007

OTHER PUBLICATIONS

Current Protocols in Molecular Biology, Hybridization Analysis of DNA Blots, pp. 2.10.8-2.10.11, 1993.*
Int'l Search Report for PCT/EP2008/004583, eight pages, completed Feb. 12, 2009.
Written Opinion for PCT/EP2008/004583, nine pages, completed Feb. 12, 2009.
Allenby et al. "Post-transcriptional regulation of the *Bacillus subtilis pst* operon encoding a phosphate-specific ABC transporter" Microbiology, vol. 150, pt. 8, pp. 2619-2628 (Aug. 2004).

(Continued)

Primary Examiner — Rosanne Kosson
(74) Attorney, Agent, or Firm — Nixon & Vanderhye P.C.

(57) ABSTRACT

The present invention relates to newly identified mRNA stabilizing elements useful for the production of a target fermentation product, such as e.g. vitamins or enzymes, in particular riboflavin (vitamin B2), biotin, pantothenic acid (vitamin B5), folic acid, thiamin, pyridoxine (vitamin B6), vitamin B12, xylanase, amylase, protease, glucanase, amylomaltase or maltogenic amylase.

4 Claims, 2 Drawing Sheets

(56) References Cited

OTHER PUBLICATIONS

Arnold et al. "mRNA stabilization by the *ompA* 5' untranslated region: Two protective elements hinder distinct pathways for mRNA degradation" RNA, vol. 4, No. 3 pp. 319-330 (Mar. 1998).

Calik et al. "Oxygen-transfer strategy and its regulation effects in serine alkaline protease production by *Bacillus licheniformis*" Biotechnol. Bioeng., vol. 69, No. 3, pp. 301-311 (Aug 2000).

Condon "RNA processing and degradation in *Bacillus subtilis*" Microbiol. Mol. Biol., vol. 67, No. 2, pp. 157-174 (Jun. 2003).

Hambraeus et al. "A 5' stem-loop and ribosome binding but not translation are important for the stability of *Bacillus subtilis aprE* leader mRNA" Microbiology, vol. 148, pt. 6, pp. 1795-1803 (Jun. 2002).

Homuth et al. "Post-transcriptional regulation of the *Bacillus subtilis dnaK* operon" Mol. Microbiol., vol. 32, No. 6, pp. 1183-1197 (Jun. 1999).

Jürgen et al. "The stability of mRNA from the *gsiB* gene of *Bacillus subtilis* is dependent on the presence of a strong ribosome binding site" Mol. Gen. Genet, vol. 258, No. 5, pp. 538-545 (Jun. 1998).

Komarova et al. "AU-rich sequences within 5' untranslated leaders enhance translation and stabilize mRNA in *Escherichia coli*" J. Bacteriol., vol. 187, No. 4, pp. 1344-1349 (Feb. 2005).

Malhotra et al. "Production and partial characterization of thermostable and calcium-independent α-amylase of an extreme thermophile *Bacillus thermooleovorans* NP54" Lett. Appl. Microbiol., vol. 31, No. 5, pp. 378-384 (Nov. 2000).

Meinken et al. "Expression of the glycolytic *gapA* operon in *Bacillus subtilis*: Differential syntheses of proteins encoded by the operon" Microbiology, vol. 149, pt. 3, pp. 751-761 (Mar. 2003).

Mueller et al. "Transcriptional regulation of *Bacillus subtilis* glucose starvation-inducible genes: Control of *gsiA* by the ComP-ComA signal transduction system" J. Bacteriol., vol. 174, No. 13, pp. 4361-4373 (Jul. 1992).

Narang & Satyanarayana "Thermostable α-amylase production by an extreme thermophile *Bacillus thermooleovorans*" Lett. Appl. Microbiol., vol. 32, No. 1, pp. 31-35 (Jan. 2001).

Narita et al. "Improvement of protein production in lactic acid bacteria using 5'-untranslated leader sequence of *slpA* from *Lactobacillus acidophilus*" Appl. Microbiol. Biotechnol., vol. 73, No. 2, pp. 366-373 (Nov. 2006).

Park et al. "*Bacillus subtilis* subtilisin gene (*aprE*) is expressed from a ($\delta^{43}$) promoter in vitro and in vivo" J. Bacteriol., vol. 171, No. 5, pp. 2657-2665 (May 1989).

Park et al. "Molecular genetic manipulation of truncated Cry1C protein synthesis in *Bacillus thuringiensis* to improve stability and yield" Appl. Environ. Microbiol., vol. 66, No. 10, pp. 4449-4455 (Oct. 2000).
Rothstein et al. "Expression of α-amylase in *Bacillus licheniformis*" J. Bacteriol., vol. 168, No. 2, pp. 839-842 (Nov. 1986).
Smolke et al. "Controlling the metabolic flux through the carotenois pathway using directed mRNA processing and stabilization" Metabolic Eng., vol. 3, No. 4, pp. 313-321 (Oct. 2001).
Sindhu et al. "Production of cellulase-free xylanase from *Bacillus megaterium* by solid state fermentation for biobleaching of pulp" Curr. Microbiol., vol. 53, No. 2, pp. 167-172 (Aug. 2006).
Skolpap et al. "Fed-batch optimization of α-amylase and protease-producing *Bacillus subtilis* using Markov chain methods" Biotechnol. Bioeng., vol. 86, No. 6, pp. 706-717 (Jun. 2004).
Tang et al. "Medium optimization for the production of thermal stable β-glucanase by *Bacillus subtilis* ZJF-1A5 using response surface methodology" Bioresource Technol., vol. 93, No. 2, pp. 175-181 (Jun. 2004).
Wetzstein et al. "Cloning, sequencing, and molecular analysis of the *dnaK* locus from *Bacillus subtilis*" J. Bacteriol., vol. 174, No. 10, pp. 3300-3310 (May 1992).

* cited by examiner

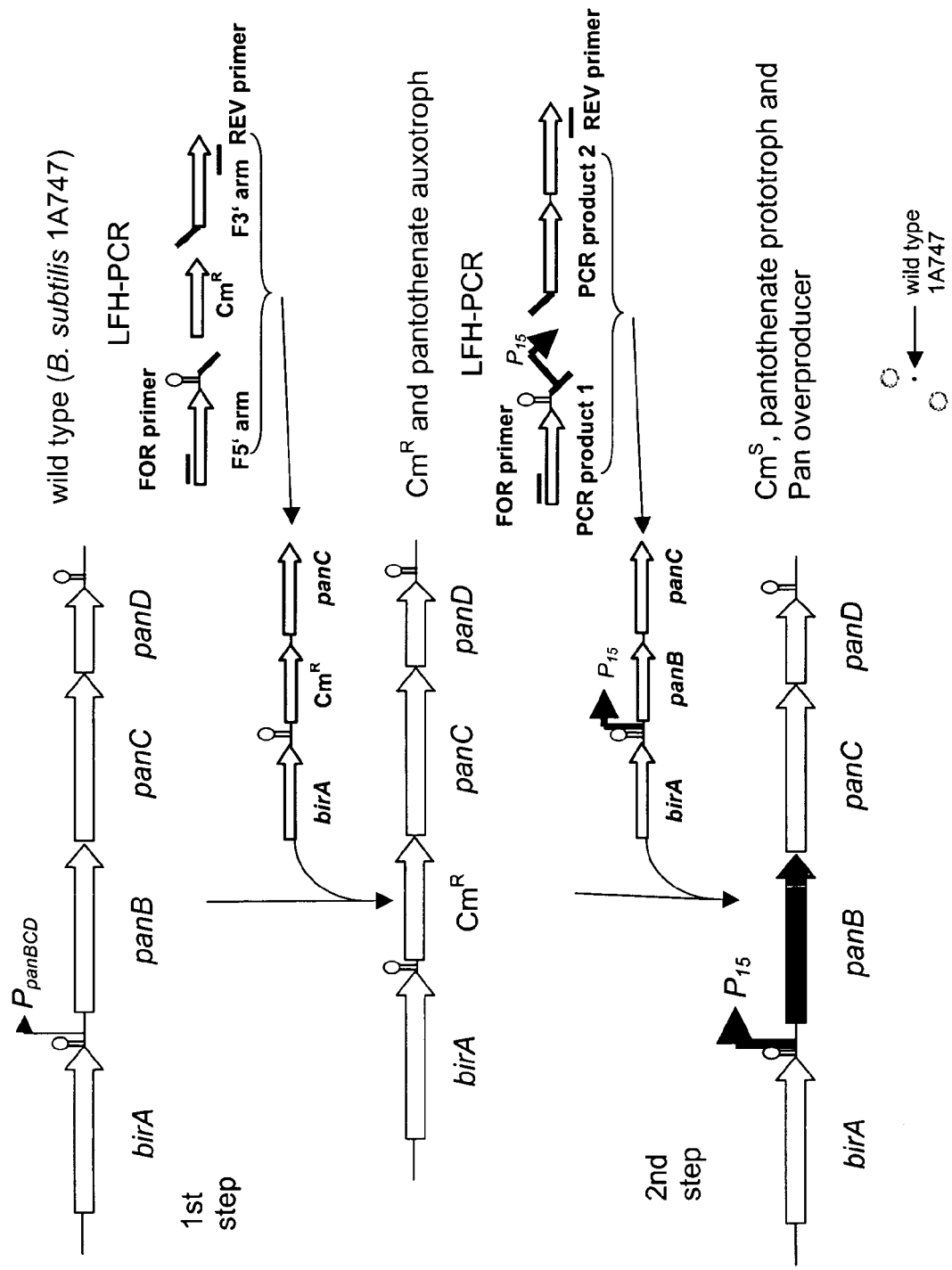

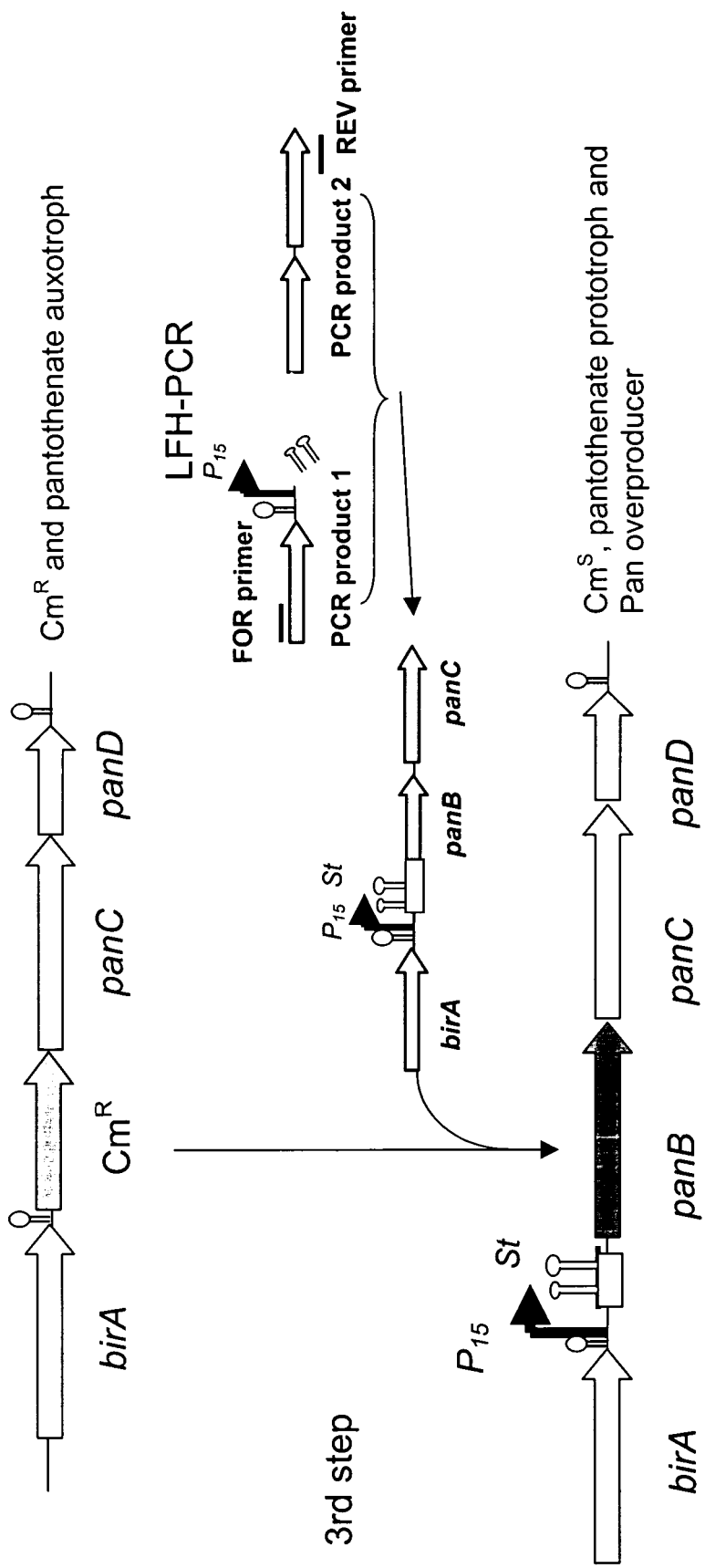

INCREASED PRODUCTION OF A TARGET PRODUCT VIA STABILIZATION OF MRNA

This application is the U.S. national phase under 35 U.S.C. 371 of International Application No. PCT/EP2008/004583, filed 9 Jun. 2008, which claims priority to EP 07011200.8, filed 7 Jun. 2007, EP 07011415.2, filed 11 Jun. 2007, and EP 07011681.9, filed 14 Jun. 2007; the entire contents of each of which are hereby incorporated by reference.

FIELD OF THE INVENTION

The present invention relates to newly identified mRNA stabilizing elements useful for the production of a target fermentation product, such as e.g. vitamins or enzymes, in particular riboflavin (vitamin B2), biotin, pantothenic acid (vitamin B5), folic acid, thiamin, pyridoxine (vitamin B6), vitamin B12, xylanase, amylase, protease, glucanase, amylomaltase or maltogenic amylase.

BACKGROUND

Many commercially valuable products are produced by fermentation reactions, such as e.g. vitamins or enzymes.

BRIEF SUMMARY OF THE INVENTION

Several methods are available for the production of target fermentation products, including e.g. replacing the natural (weak) promoter by a strong promoter or amplification of expression cassettes within the chromosome, said cassette containing a single promoter operably linked to a gene of interest and an amplifiable selectable marker gene, e.g. an antibiotic resistance marker. The amplification leads to the production of multiple copies of the expression cassette and the selectable marker gene in the chromosome. One could also increase the amount of a desired fermentation product by decoupling the production of the desired product from the growth of said host cell.

However, there are disadvantages associated with the above-mentioned approaches. For example, it may not be possible to achieve saturating levels of mRNA by amplification of genes driven by a single promoter. Furthermore, the production of multiple copies of the expression cassette and the selectable marker gene in the chromosome of a host cell may not be stable or might even prevent further expression of the respective gene (feedback inhibition).

It is an object of the present invention to improve the yield and/or productivity of a target fermentation product, in particular the production of vitamins or enzymes.

Surprisingly, it has now been found that the production of a target fermentation product could be enhanced by increasing the transcript stability, i.e. stabilization of mRNA generated via transcription of the respective gene(s) involved in the biosynthesis of such target fermentation products.

In particular, it has now been found that the introduction of a polynucleotide having a nucleotide sequence that hybridizes preferably under highly stringent conditions to a sequence shown in SEQ ID NO:1 to 5 plays an important role in stabilization of mRNA transcribed from a respective gene. The mRNA stabilizing element may be introduced downstream of the transcription start of a respective target gene. It has also been found that by introducing said polynucleotide or mRNA stabilizing element into a suitable microorganism, such as for example *Bacillus*, the production of a target fermentation product can be greatly improved due to stabilized mRNA transcripted from the respective gene(s) involved in production of the desired target product.

The target fermentation products may be selected from vitamins or enzymes. In the case of vitamins, the target fermentation product is particularly selected from the group consisting of riboflavin (vitamin B2), biotin, pantothenic acid (vitamin B5), folic acid, thiamin and pyridoxine (vitamin B6). In the case of enzymes, the target fermentation product is particularly selected from the group consisting of transferases [EC 2] and hydrolases [EC 3], preferably selected from glycosyltransferases [EC 2.4], glycosylases [EC 3.2] or peptidases [EC 3.4], more preferably selected from glycosidases [EC 3.2.1] or hexosyltranferases [EC 2.4.1], such as e.g. α-amylase, xylanase, β-glucanase, maltogenic amylase (glucan 1,4-α-maltohydrolase), neutral protease/proteinase or amylomaltase (4-α-glucanotransferase).

DETAILED DESCRIPTION OF THE INVENTION

In one embodiment, the present invention is directed to fermentative production of riboflavin (vitamin B2). As used herein, the term "riboflavin" includes but is not limited to riboflavin, flavin mononucleotide (FMN), flavin adenine dinucleotide (FAD), as well as precursors, derivatives and salts of riboflavin, FMN or FAD, such as e.g. riboflavin-5-phosphate or sodium riboflavin-5-phosphate. Precursors and/or derivatives of riboflavin, FMN and FAD may be selected from e.g. DRAPP; 5-amino-6-ribosylamino-2,4 (1H,3H)-pyrimidinedione-5'-phosphate; 2,5-diamino-6-ribitylamino-4 (3H)-pyrimidinone-5'-phosphate; 5-amino-6-ribitylamino-2,4 (1H,3H)-pyrimidinedione-5'-phosphate; 5-amino-6-ribitylamino-2,4 (1H,3H)-pyrimidinedione; 6,7-dimethyl-8-ribityllumazine (DMRL); and flavoproteins. The terms "riboflavin" and "vitamin B2" are used interchangeably herein. The genes involved in biosynthesis of riboflavin as well as methods for fermentative production of riboflavin are known (see e.g. EP 405370 or Ullman's Encyclopedia of Industrial Chemistry, 7$^{th}$ Edition, 2007, Chapter Vitamins). These methods may be also applied for production of riboflavin using an mRNA stabilizing element as described herein.

The *B. subtilis* riboflavin (rib) operon consists of the medium strong $P_{rib}$ promoter, a 5' leader sequence containing a so-called riboswitch and the genes ribD (ribG), ribE (ribB), ribA, ribH, and ribT. Beside RibT, the function and catalytic activity of all gene products is known. The riboswitch of the 5' leader sequence is able to bind flavin monophosphate (FMN). After FMN binding a refolding of the leader prevents further transcription of the five genes in the rib operon. In the absence of FMN the structure of the riboswitch allows the transcription of the five rib genes and consequently the synthesis of riboflavin.

In one embodiment, the present invention is directed to fermentative production of biotin. As used herein, the term "biotin" includes but is not limited to biotin, precursors and/or derivatives of biotin. Examples of such precursors are selected from pimelic acid, pimelyl-CoA, 7-keto-8-aminopelargonic acid (7-KAP), 7,8-diamino-pelargonic acid (DAPA) or dethiobiotin (DTB). The genes involved in biosynthesis of biotin as well as methods for fermentative production of biotin are known (see e.g. EP 635572 or EP 892066 or Ullman's Encyclopedia of Industrial Chemistry, 7$^{th}$ Edition, 2007, Chapter Vitamins). These methods may be also applied for production of biotin using an mRNA stabilizing element as described herein.

In a further embodiment, the target fermentation product is pantothenic acid (vitamin B5). As used herein, the term "pantothenic acid" includes but is not limited to pantothenic acid, precursors and/or derivatives thereof such as salts or esters thereof, i.e. pantothenate, in particular calcium pantothenate, or the alcohol form of pantothenic acid, i.e. pantothenol or panthenol. The terms "pantothenic acid", "pantothenate" and "vitamin B5" are used interchangeably herein. Precursors/intermediates in the biosynthetic pathway of pantothenic acid which are included may be selected from e.g. pantoate, α-ketopantoate or α-ketoisovalerate. The genes involved in biosynthesis of pantothenic acid as well as methods for fermentative production of pantothenic acid are known (see e.g. WO 01/21772, WO 02/057474, WO 02/061108 or Ullman's Encyclopedia of Industrial Chemistry, 7$^{th}$ Edition, 2007, Chapter Vitamins). These methods may be also applied for production of pantothenic acid using an mRNA stabilizing element as described herein.

In another embodiment, the target fermentation product is folic acid. As used herein, the term "folic acid" includes but is not limited to folic acid and precursors/derivatives thereof, such as e.g. folate, guanosine 5'-triphosphate (GTP), p-aminobenzoic acid, L-glutamic acid, dihydroneopterin tri-/mono-phosphate, dihydroneopterin, hydroxymethyldihydropterin, hydroxymethyldihydropterin pyrophosphate, dihydropteric acid, and dihydrofolic acid. The genes involved in biosynthesis of folic acid as well as methods for fermentative production of folic acid are known (see e.g. Ullman's Encyclopedia of Industrial Chemistry, 7$^{th}$ Edition, 2007, Chapter Vitamins). These methods may be also applied for production of folic acid using an mRNA stabilizing element as described herein.

In a further embodiment, the target fermentation product is thiamin. As used herein, the term "thiamin" includes but is not limited to thiamin, thiamin monophosphate (TMP), thiamin pyrophosphate and precursors/derivatives thereof, such as, e.g. 4-amino-5-hydroxymethyl-2-methylpyrimidine (HMP), 5-(2-hydroxyethyl)-4-methylthiazole (HET) and a combination thereof. Furthermore included are precursors and/or derivatives of the HMP and/or HET-pathway, such as e.g. glycine, cysteine, isoleucine, threonine, 5-aminoimidazole ribotide (AIR) or 4-amino-2-methyl-5-pyrimidinemethaneamine (Grewe Diamine). The genes involved in biosynthesis of thiamin as well as methods for fermentative production of thiamin are known (see e.g. WO 2004/106557 or Ullman's Encyclopedia of Industrial Chemistry, 7$^{th}$ Edition, 2007, Chapter Vitamins). These methods may be also applied for production of thiamin using an mRNA stabilizing element as described herein.

In one embodiment, the target fermentation product is pyridoxine (vitamin B6). As used herein, the term "pyridoxine" includes but is not limited to pyridoxine, pyridoxol, pyridoxal, pyridoxamine and precursors/derivatives thereof such as e.g. pyridoxal 5'-phosphate. The terms "pyridoxine" and "vitamin B6" are used interchangeably herein. The genes involved in biosynthesis of pyridoxine as well as methods for fermentative production of pyridoxine are known (see e.g. Mittenhuber, J. Mol. Microbiol. Biotechnol. 3(1), p. 1-20, 2001 or EP 950715 or Ullman's Encyclopedia of Industrial Chemistry, 7th Edition, 2007, Chapter Vitamins). These methods may be also applied for production of pyridoxine using an mRNA stabilizing element as described herein.

The target fermentation product may also be selected from enzymes, in particular selected from the group consisting of transferases [EC 2] and hydrolases [EC 3], preferably selected from glycosyltransferases [EC 2.4], glycosylases [EC 3.2] or peptidases [EC 3.4], more preferably selected from glycosidases [EC 3.2.1] or hexosyltranferases [EC 2.4.1], such as e.g. α-amylase, xylanase, β-glucanase, maltogenic amylase (glucan 1,4-α-maltohydrolase), neutral protease/proteinase or amylomaltase (4-α-glucanotransferase). The genes involved in biosynthesis of said enzymes as well as methods for fermentative production thereof are known (see e.g. WO 03/062409 or EP 585617 or WO 97/06181 or Sonenshein, Hoch, Losick (eds.): *Bacillus subtilis* and Other Gram-Positive Bacteria: Biochemistry, Physiology, and Molecular Genetics, ASM Press, 1993 or Ullman's Encyclopedia of Industrial Chemistry, 7$^{th}$ Edition, 2007, Chapter Enzymes). These methods may be also applied for production of enzymes using an mRNA stabilizing element as described herein.

Consequently, the invention relates to the use of a polypeptide for the production of a target fermentation product, said polynucleotide being selected from the group consisting of:
(a) polynucleotides comprising the nucleotide sequence according to SEQ ID NO:1 to 5;
(b) polynucleotides comprising a nucleotide sequence obtainable by nucleic acid amplification such as polymerase chain reaction, using genomic DNA from a microorganism as a template and a primer set according to SEQ ID NO:6/SEQ ID NO:7, SEQ ID NO:8/SEQ ID NO:9, SEQ ID NO:10/SEQ ID NO:11, SEQ ID NO:12/SEQ ID NO:13 and SEQ ID NO:14/SEQ ID NO:15, respectively;
(c) polynucleotides comprising a nucleotide sequence which is a fragment or derivative of a polynucleotide according to (a) or (b), said fragment or derivative having the activity of an mRNA stabilizing element;
(d) polynucleotides the complementary strand of which hybridizes under stringent conditions to a polynucleotide as defined in any one of (a) to (c) and which have the activity of an mRNA stabilizing element; and
(e) polynucleotides which are at least 60%, such as 70, 85, 90 or 95% identical to a polynucleotide as defined in any one of (a) to (c) and which have the activity of an mRNA stabilizing element
or
the complementary strand of such a polynucleotide.

In particular, the invention relates to a process for the production of a target fermentation product with a microorganism wherein said microorganism is incubated in a aqueous medium under conditions that allow the production of said target fermentation product from a carbon source and wherein optionally the target fermentation product is isolated as the fermentation product, wherein said microorganism is genetically altered by introduction of a polynucleotide that leads to an improved yield and/or efficiency of production of the target fermentation product produced by said microorganism, said polynucleotide being selected from the group consisting of:
(a) polynucleotides comprising the nucleotide sequence according to SEQ ID NO:1 to 5;
(b) polynucleotides comprising a nucleotide sequence obtainable by nucleic acid amplification such as polymerase chain reaction, using genomic DNA from a microorganism as a template and a primer set according to SEQ ID NO:6/SEQ ID NO:7, SEQ ID NO:8/SEQ ID NO:9, SEQ ID NO:10/SEQ ID NO:11, SEQ ID NO:12/SEQ ID NO:13 and SEQ ID NO:14/SEQ ID NO:15, respectively;
(c) polynucleotides comprising a nucleotide sequence which is a fragment or derivative of a polynucleotide according to (a) or (b), said fragment or derivative having the activity of an mRNA stabilizing element;
(d) polynucleotides the complementary strand of which hybridizes under stringent conditions to a polynucleotide as defined in any one of (a) to (c) and which have the activity of an mRNA stabilizing element; and (e) polynucleotides which are at least 60%, such as 70, 85, 90 or 95% identical to a polynucleotide as defined in any one of (a) to (c) and which have the activity of an mRNA stabilizing element
or
the complementary strand of such a polynucleotide.

The nucleic acid sequence as disclosed herein and as isolated from *Bacillus subtilis* shown in SEQ ID NO:1 to 5 was found to be particularly useful in stabilization of mRNA and thus helpful in the production of a target fermentation product as described above in a microorganism, in particular bacteria, such as Gram-positive and Gram-negative bacteria, such as for instance *Bacillus*.

The term "mRNA stabilizing element" as used herein refers to a DNA sequence which upon introduction in the 5'-untranslated region, e.g. downstream of the transcription start of the respective gene, is capable of providing an increase stability to the mRNA which is transcribed from the respective gene comprising said "mRNA stabilizing element". The mRNA stabilizing element preferably contains 1 or more stem loops but may also contain no loop at all.

The present invention provides stabilized mRNA sequences. The stabilized mRNA is transcribed from an endogenous gene containing a DNA sequence as defined above which is introduced downstream of the transcription start of the relevant gene(s). This gene may be involved in production of a desired target fermentation product as described above. The mRNA stabilizing element may be introduced directly downstream of the transcription start or 1 or more nucleotides downstream thereof. Introduction of said mRNA stabilizing element has the effect that the mRNA is no longer or less accessible to enzymatic degradation and thus results in higher production/yield/efficiency of the desired target fermentation product.

Any nucleic acid sequence capable of forming one or more stem loop(s) leading to increased stability of mRNA transcripts from one or more target gene(s) which are preferably involved in the production of a desired target fermentation product as defined above may be within the scope of the present invention. Stabilization of mRNA may also be possible via a strong ribosome binding site (RBS) which does not necessarily form a loop, as e.g. in the case of SEQ ID NO:5 or SEQ ID NO:20.

Thus, the present invention relates to mRNA stabilizing elements introduced at the 5'-end of an endogenous gene which upon transcription result in stabilized mRNA transcripts, i.e. which are capable of increasing the stability of mRNA transcripts.

A nucleic acid according to the invention may be obtained by nucleic acid amplification using e.g., cDNA, mRNA or alternatively, genomic DNA as a template and appropriate oligonucleotide primers such as the nucleotide primers according to SEQ ID NO:6/SEQ ID NO:7, SEQ ID NO:8/SEQ ID NO:9, SEQ ID NO:10/SEQ ID NO:11, SEQ ID NO:12/SEQ ID NO:13 and SEQ ID NO:14/SEQ ID NO:15, respectively, according to standard PCR amplification techniques, such as for instance according to the process described in Example 1. The nucleic acid thus amplified may be cloned into an appropriate vector and characterized by DNA sequence analysis. Synthetic DNA may also be used as template for such PCR.

The template DNA may be derived from the same or a different host cell to be used for the production of the desired target fermentation product. Furthermore, the template for the reaction may be cDNA obtained by reverse transcription of mRNA prepared from strains known or suspected to comprise a polynucleotide according to the invention. The PCR product may be subcloned and sequenced to ensure that the amplified sequences represent the sequences of a new nucleic acid sequence as described herein, or a functional equivalent thereof. Furthermore, a nucleic acid sequence according to the present invention may be completely or partly synthesized using methods well-known in the art.

Accordingly, the invention relates to polynucleotides and their use for the production of a target fermentation product as defined herein comprising a nucleotide sequence obtainable by nucleic acid amplification such as polymerase chain reaction, using DNA such as genomic DNA from a microorganism as a template and a primer set according to SEQ ID NO:6/SEQ ID NO:7, SEQ ID NO:8/SEQ ID NO:9, SEQ ID NO:10/SEQ ID NO:11, SEQ ID NO:12/SEQ ID NO:13 and SEQ ID NO:14/SEQ ID NO:15, respectively.

The invention also relates to polynucleotides and their use for the production of a target fermentation product as defined herein comprising a nucleotide sequence which is a fragment or derivative of a polynucleotide as described herein, said fragment or derivative having the activity of an mRNA stabilizing element. An example of such a fragment is shown in SEQ ID NO:16, 17, 18, 19 and/or 20.

The invention also relates to polynucleotides and their use for the production of a target fermentation product as defined herein the complementary strand of which hybridizes under stringent conditions to a polynucleotide as defined herein and which have the activity of an mRNA stabilizing element.

The invention also relates to polynucleotides and their use for the production of a target fermentation product as defined herein which are at least 60% identical to a polynucleotide as defined herein and which have the activity of an mRNA stabilizing element; and the invention also relates to polynucleotides being the complementary strand of a polynucleotide as defined herein above.

The invention also relates to primers, probes and fragments that may be used to amplify or detect a DNA according to the invention as well as their use for the production of a target fermentation product as defined herein The mRNA stabilizing elements as defined above may be of any length but preferably consist of at least 15 nucleotides, more preferably at least 20, 30, 40, 50, 60, 70, 80, 90, 100 nucleotides, most preferably 39-87 nucleotides comprising preferably 1 or more stem loops, in particular 1 or 2 stem loops. The stem may consist of at least 4 base pairs, preferably at least 8, 10, 12, 15 base pairs (with mismatch nucleotides/interior loops and/or bulge loops possibly being present) and the loops may consist of e.g. 3-30 unbounded nucleotides, preferably 4, 6, 8, 10, 11, 14, 15, 25 or more nucleotides. The length of the interior loops is preferably 2, 4, 6, 8, 10, 12 unbounded nucleotides. One or more bulge loop(s) may be present, consisting of e.g. 1, 2 or even 6 unbounded nucleotides. The calculated thermodynamic stability ($\Delta G$) of the stem loop may be calculated according to algorithms developed by Zuker (2003, Nucleic Acids Res. 31:3406-3415). In one embodiment, the calculated thermodynamic stability is $-2.8$ kcal/mol or lower, preferably $-3, -4, -5, -6, -7, -8, -9, -10, -11, -12, -15, -20$ kcal/mol or lower. In another embodiment of the present invention, the mRNA stabilizing elements may comprise no loop at all.

The invention also relates to processes for producing microorganisms genetically engineered with a polynucleotide as defined above which are capable of producing an mRNA transcript with increased and/or improved stability.

The invention also relates to microorganisms, which are genetically engineered with the nucleic acid sequences as defined above as well as to processes for producing said genetically engineered cells.

The invention also relates to genetically engineered microorganisms wherein the yield and/or efficiency of production of a target fermentation product as defined above is improved and/or enhanced and to microorganisms wherein the stability of an mRNA transcripted from a gene involved in the biosynthetic pathway of a target fermentation product as defined above is increased and/or improved so that the yield of the target fermentation product which is produced from a carbon source is increased.

Furthermore, the invention is related to the use of nucleic acid sequences, e.g. mRNA stabilizing elements as defined above or to the use of a genetically engineered microorganism for the production of a target fermentation product as defined above.

The skilled person will know how to generate such genetically engineered cells, in particular microorganisms, i.e. how to introduce a DNA sequence of the present invention as defined above leading to stabilized transcripts. Introduction of a DNA sequence as used herein may be for instance addition or insertion of a DNA sequence by transformation, conjugation or transduction into the chromosome of a host cell. Said addition or insertion may occur by DNA recombination that may or may not also result in a removal or deletion of chromosomal DNA nucleotides. Methods by which introduction of DNA sequences into a host cell, e.g. microorganisms, are achieved, especially by site-specific introduction, are well-known in the art and described in e.g. Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.). The DNA sequence capable of forming one or more stem loops may be introduced downstream of the transcription start, in particular at least 1, 2, 3, 5, 6, 7 or more, e.g. 8, 9, 10, 11, 12, 13 nucleotides downstream of the transcription start site of the relevant gene(s) involved in biosynthesis of a desired target fermentation product. The number and kind of nucleotide changes are limited by the fact that no sequence is formed representing an RNase E-specific nuclease cleaving site. The same method also applies to elements which do not form any loop.

The stability of mRNA transcripts may be for instance measured by determination of the mRNA half-life using Northern blot and/or real-time PCR stabilization as described e.g. by Allenby et al., Microbiology, 150, p. 2619-2628 (2004) or Sharp and Bechhofer, Mol. Microbiol. 57, 484-495 (2005). As used herein, the mRNA stability is increased (or mRNA degradation is reduced/blocked) if the half-life of said mRNA is increased by at least 1%, 2%, 5%, 10%, 25%, 50%, 75%, 100%, 200% or even more than 500%, compared to mRNA half-life transcribed from a wild-type gene, i.e. not containing an mRNA stabilizing element as of the present invention.

The invention may be performed in/with any microorganism carrying the gene(s) involved in the biosynthesis of the above-defined target fermentation products. Suitable microorganisms may be selected from e.g. bacteria, fungi (including yeast) and algae. The term "bacteria" includes both Gram-negative and Gram-positive microorganisms. Suitable bacteria may be selected from e.g. *Escherichia, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus* or *Streptomyces*. Preferably, the microorganism or host cell is selected from the group consisting of *B. subtilis, B. amyloliquefaciens, B. licheniformis, B. puntis, B. halodurans, B. pumilus, G. oxydans, Rhodobacter sphaeroides* and *Pseudomonas zeaxanthinifaciens, Paracoccus denitrificans, E. coli, C. glutamicum, Streptomyces lividans, Sinorhizobium melioti* and *Rhizobium radiobacter*. Examples of yeasts are *Saccharomyces*, particularly *S. cerevisiae, Pichia* or *Candida*. Examples of preferred other fungi are *Aspergillus* and *Pencillium*, in particular *A. niger* and *P. chrysogenum*.

Microorganisms which can be used for the present invention may be publicly available from different sources, e.g., Deutsche Sammlung von Mikroorganismen und Zellkulturen (DSMZ), Inhoffenstrasse 7B, D-38124 Braunschweig, Germany, American Type Culture Collection (ATCC), P.O. Box 1549, Manassas, Va. 20108 USA, Agricultural Research Culture Collection (NRRL), Peoria, Ill., USA, Culture Collection Division, NITE Biological Resource Center, 2-5-8, Kazusakamatari, Kisarazu-shi, Chiba, 292-0818, Japan (formerly: Institute for Fermentation, Osaka (IFO), 17-85, Jusohonmachi 2-chome, Yodogawa-ku, Osaka 532-8686, Japan) or from the *Bacillus* Genetic Stock Center (BGSC), The Ohio State University, Columbus, Ohio 43210 USA. An example of a preferred bacterium is for instance *B. subtilis* 1A747 obtainable from BGSC, which is a derivative of *B. subtilis* 168.

In connection with the above process using a microorganism it is understood that the above-mentioned microorganisms also include synonyms or basonyms of such species having the same physiological properties, as defined by the International Code of Nomenclature of Prokaryotes. The nomenclature of the microorganisms as used herein is the one officially accepted (at the filing date of the priority application) by the International Committee on Systematics of Prokaryotes and the Bacteriology and Applied Microbiology Division of the International Union of Microbiological Societies, and published by its official publication vehicle International Journal of Systematic and Evolutionary Microbiology (IJSEM).

Examples of preferred strains for the production of e.g. riboflavin are selected from *B. subtilis, B. licheniformis, B. amyloliquefaciens, B. ammoniagenes, E. coli* and *C. glutamicum*. A more preferred strain is *B. subtilis* RB50:: [pRF69]$_n$ containing multiple (n) copies (for example about 5 to about 20 copies) of pRF69 encoding a rib operon modified with the strong phage SPO1 promoter ($P_{15}$) to enhance transcription of the rib genes (see e.g. EP 405370 and Perkins et al., J. Ind. Microbiol. Biotechnol., 22:8-18, 1999 for construction of the strain and culture conditions to result in riboflavin production). *B. subtilis* RB50 and plasmid pRF69 may be available from NRRL (accession number B 18502) and from ATCC (accession number ATCC 68338), respectively. Thus, in one embodiment the above-mentioned preferred strains such as, e.g. *B. subtilis, B. licheniformis, B. amyloliquefaciens, B. ammoniagenes, E. coli* or *C. glutamicum* are genetically altered by introduction of an mRNA stabilizing element such as, e.g. identified in SEQ ID NOs:1-5 and the such altered strains are used for production of riboflavin. Construction of such a strain is performed as exemplified in FIG. 1, wherein the genes of the pantothenate operon (panB, panC, panD) are replaced by the corresponding genes of the riboflavin operon (see e.g. Examples 1 and 2).

Examples of preferred strains for production of e.g. biotin are selected from *B. subtilis, B. sphaericus* and *E. coli*, more preferably strains available from ATCC, such as e.g. *B. subtilis* PA3, HB43, HB3, BI544, BI535, BI421, BI304, BI282, and BI274 (accession numbers ATCC 55567 to ATCC 55575) as disclosed in EP 635572. Thus, in one embodiment the above-mentioned preferred strains such as, e.g. *B. subtilis, B. sphaericus* or *E. coli* are genetically altered by introduction of an mRNA stabilizing element such as, e.g. identified in SEQ ID NOs:1-5 and the such altered strains are used for production of biotin. Construction of such a strain is performed as exemplified in FIG. 1, wherein the genes of the pantothenate operon (panB, panC, panD) are replaced by the corresponding genes of the biotin operon (for more details, see e.g. Examples 1 and 2).

Examples of preferred strains for production of e.g. pantothenic acid are selected from *B. subtilis*, such as *B. subtilis* 168, *B. licheniformis, B. amyloliquefaciens, B. puntis, B. halodurans* and *C. glutamicum*. Thus, in one embodiment the above-mentioned preferred strains such as, e.g. *B. subtilis* 168, *B. licheniformis, B. amyloliquefaciens, B. puntis, B. halodurans* or *C. glutamicum* are genetically altered by introduction of an mRNA stabilizing element such as, e.g. identified in SEQ ID NOs:1-5 and the such altered strains are used for production of pantothenic acid. Construction of such a strain is performed as exemplified in FIG. 1.

Examples of preferred strains for production of e.g. thiamin are selected from *B. subtilis* and *E. coli*, more preferably strains as deposited under the terms of the Budapest treaty with ATCC and DSMZ, respectively, such as e.g. *B. subtilis* TH95, *B. subtilis* TH101, *B. subtilis* TH115, *B. subtilis* TH116 (accession numbers ATCC PTA-5221 to ATCC PTA-5224) or *B. subtilis* TH404 and *B. subtilis* TH405 (accession numbers DSM 16333 and 16334). Thus, in one embodiment the above-mentioned preferred strains such as, e.g. *B. subtilis* or *E. coli* are genetically altered by introduction of an mRNA stabilizing element such as, e.g. identified in SEQ ID NOs:1-5 and the such altered strains are used for production of thiamin. Construction of such a strain is performed as exemplified in FIG. 1, wherein the genes of the pantothenate operon (panB, panC, panD) are replaced by the corresponding genes involved in thiamin biosynthesis (for more details, see e.g. Examples 1 and 2). Genes involved in thiamin biosynthesis are known, see e.g. Schyns et al., Journal Bacteriology, vol. 187, No. 23, pp. 8127-8136, 2005).

Examples of preferred strains for production of e.g. pyridoxine are selected from *B. subtilis, E. coli, S. melioti, P. putida, L. brevis, F. indolgenes, C. ammoniagenes, C. glutamicum, P. guilliermondii, S. cerevisiae, C. tropicalis, E. cloacae, P. maltophila*, more preferably strains available from NITE Biological Resource Center such as e.g. *Sinorhizobium melioti* (accession number IFO 14782 or DSM 10226), *Flavobacterium indologenes* (accession number IFO 14944), *Lactobacillus brevis* (accession number IFO 13110), *Bacillus subtilis* (accession number IFO 3007), *Klebsiella planticola* (accession number IFO 3317), *Escherichia coli* (accession number IFO 13168), *Pseudomonas putida* (accession number IFO 3738), *Pseudomonas maltophila* (accession number IFO 12692), *Enterobacter cloacae* (accession number IFO 3320), *Corynebacterium ammoniagenes* (accession number IFO 12612), *Corynebacterium glutamicum* (accession number IFO 12168), *Brevibacterium acetylicum* (accession number IFO 12146), *Pichia guilliermondii* (accession number IFO 10106), *Saccharomyces cerevisiae* (accession numbers IFO 0304 and IFO 0306) and *Candida tropicalis* (accession numbers IFO 0199 and IFO 0587). Thus, in one embodiment the above-mentioned preferred strains such as, e.g. *B. subtilis, E. coli, S. melioti, P. putida, L. brevis, F. indolgenes, C. ammoniagenes, C. glutamicum, P. guilliermondii, S. cerevisiae, C. tropicalis, E. cloacae* or *P. maltophila* are genetically altered by introduction of an mRNA stabilizing element such as, e.g. identified in SEQ ID NOs:1-5 and the such altered strains are used for production of pyridoxine. Construction of such a strain is performed as exemplified in FIG. 1, wherein the genes of the pantothenate operon (panB, panC, panD) are replaced by the corresponding genes involved in pyridoxine biosynthesis (for more details, see e.g. Examples 1 and 2). Genes involved in pyridoxine biosynthesis are known, see e.g. Mittenhuber, Journal Mol. Microbiol. Biotechnol. 3(1), pp. 1-20, 2001.

Examples of preferred strains for production of enzymes such as e.g. transferases [EC 2] or hydrolases [EC 3] are selected from *B. licheniformis, B. amyloliquefaciens*, and *B. subtilis*. In one embodiment, said strains are genetically altered by introduction of an mRNA stabilizing element such as, e.g. identified in SEQ ID NOs:1-5 and such altered strains are used for production of enzymes such as, e.g. transferases or hydrolases. Construction of such a strain is performed as exemplified in FIG. 1 wherein the genes of the pantothenate operon (panB, panC, panD) are replaced by the respective genes encoding said enzymes or according to Example 3.

The invention also relates to processes for the expression of endogenous gene(s) involved in the biosynthesis of a target fermentation product as e.g. defined above within a microorganism, wherein the mRNA transcribed from said gene(s) has increased stability. This increased stability is achieved through introduction of an mRNA stabilizing element as defined above into the microorganism. As a result, the mRNA thus generated is more stable than the mRNA generated from the corresponding wild-type gene.

The present invention is also related to the production of microorganisms capable of producing the target fermentation product, wherein the productivity and/or yield of said target fermentation product is increased compared to the wild-type organism. This increase is obtained via altering said microorganism by introduction of a polynucleotide as of the present invention so that the microorganism produces a more stable mRNA.

Thus, the present invention is directed to a process for the production of a target fermentation product with a microorganism wherein said microorganism is incubated in an aqueous medium under conditions that allow the production of said target fermentation product from a carbon source and wherein optionally the target fermentation product is isolated as the fermentation product, wherein said microorganism is genetically altered by introduction of a polynucleotide as defined above that it leads to an improved yield and/or efficiency of production of the target fermentation product produced by said microorganism.

Furthermore, the present invention discloses a process for the production of mRNA with increased stability transcribed from a gene involved in the biosynthetic pathway of a target fermentation product in a microorganism, said microorganism comprising a polynucleotide as defined above introduced downstream of the transcription start of the respective gene(s). Suitable microorganisms and putative target gene(s) are listed above.

As a further embodiment, the present invention is related to a process for the production of a microorganism capable of producing a target fermentation product, said process comprising the step of altering said microorganism by introduction of a polynucleotide as defined above so that the microorganism produces a stabilized mRNA leading to an improved yield and/or efficiency of production of the target fermentation product produced by said microorganism as well as to a process for the production of a microorganism wherein the stability of mRNA transcribed from an endogenous gene is increased, comprising the step of altering said microorganism by introduction of a polynucleotide as defined above downstream of the transcription start of the respective endogenous gene.

All these processes may comprise the step of altering a microorganism, wherein "altering" as used herein encompasses the process for "genetically altering" in such a way that (i) the yield and/or productivity of the fermentation product and/or (ii) the stability of an mRNA transcript can be improved compared to the wild-type organism. This is achieved by introducing a nucleic acid sequence as defined above into the respective organism.

The term "genetically engineered" or "genetically altered" means the scientific alteration of the structure of genetic material in a living organism. It involves the production and use of recombinant DNA. More in particular it is used to delineate the genetically engineered or modified organism from the naturally occurring organism. Genetic engineering may be done by a number of techniques known in the art, such as e.g. gene replacement, gene amplification, gene disruption, addition, insertion, deletion, transfection, transformation using plasmids, viruses, or other vectors. A genetically modified organism, e.g. genetically modified microorganism, is also often referred to as a recombinant organism, e.g. recombinant microorganism.

The nucleic acid sequence as defined in SEQ ID NO:1 to 5 was determined by sequencing a genomic clone obtained from B. subtilis.

The invention also relates to fragments and/or derivatives of a nucleotide sequence according to SEQ ID NO:1, 2, 3, 4 and/or 5 having the activity of an mRNA stabilizing element, i.e. leading to transcripts which are more stable than a wild-type mRNA. Said fragments/derivatives may consist of 1 or more, in particular 1 or 2, stem-loop(s). An example of such a fragment is shown in SEQ ID NO:16, 17, 18, or 19. Such fragments may also consist of no loop at all as exemplified in SEQ ID NO:20.

The nucleic acids of the present invention are preferably provided in an isolated form, and preferably purified to homogeneity.

The term "isolated" means that the material is removed from its original environment (e.g., the natural environment if it is naturally occurring). For example, a naturally-occurring polynucleotide present in a living microorganism is not isolated, but the same polynucleotide, separated from some or all of the coexisting materials in the natural system, is isolated. Such polynucleotides could be part of a vector and/or such polynucleotides could be part of a composition and still be isolated in that such vector or composition is not part of its natural environment.

As used herein, the term "gene" refers to nucleic acid molecules which may be isolated from chromosomal DNA, which include an open reading frame encoding a protein, e.g. proteins involved in the synthesis of the desired target fermentation product, such as for instance enzymes from the B. subtilis riboflavin biosynthetic pathway.

A gene may include coding sequences, non-coding sequences such as for instance untranslated sequences located at the 3'- and 5'-ends of the coding region of a gene, such as for instance promoter regions, regulator regions and terminator regions important for the appropriate expression and stabilization of the polypeptide derived thereof.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule may be single-stranded or double-stranded, but preferably is double-stranded DNA. The nucleic acid may be synthesized using oligonucleotide analogs or derivatives (e.g., inosine or phosphorothioate nucleotides). Such oligonucleotides may be used, for example, to prepare nucleic acids that have altered base-pairing abilities or increased resistance to nucleases.

Unless otherwise indicated, all nucleotide sequences determined by sequencing a DNA molecule herein were determined using an automated DNA sequencer. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence may be more precisely determined by other approaches including manual DNA sequencing methods well known in the art.

The person skilled in the art is capable of identifying such erroneously identified bases and knows how to correct for such errors.

A nucleic acid molecule according to the invention may comprise only a portion or a fragment of the nucleic acid sequence provided by the present invention, such as for instance the sequence shown in SEQ ID NO:1 to 5, for example a fragment which may be used as a probe or primer such as for instance SEQ ID NO:6, 7, 8, 9, 10, 11, 12, 13, 14 or 15 or a fragment consisting of the stem and one or more loops of the mRNA stabilizing element, such as e.g. shown in SEQ ID NO:16, 17, 18 or 19, or a fragment without a loop, such as e.g. shown in SEQ ID NO:20. The probe/primer typically comprises substantially purified oligonucleotides which typically comprises a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequence shown in SEQ ID NO:1, 2, 3, 4, 5 or a fragment or derivative thereof.

A nucleic acid molecule encompassing all or a portion of the nucleic acid sequence of SEQ ID NO:1 may be also isolated by the polymerase chain reaction (PCR) using synthetic oligonucleotide primers designed based upon the sequence information contained herein.

The invention also relates to an isolated polynucleotide hybridizable under stringent conditions, preferably under highly stringent conditions, to a polynucleotide as of the present invention, such as for instance a polynucleotide shown in SEQ ID NO:1 to 5. Advantageously, such polynucleotide may be obtained from a microorganism capable of producing the above-defined target fermentation product, in particular Bacillus subtilis.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

In one embodiment, a nucleic acid of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence shown in SEQ ID NO:1 or the complement thereof.

A preferred, non-limiting example of stringent hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include incubations at 42° C. for a period of several days, such as 2-4 days, using a labeled DNA probe, such as a digoxygenin (DIG)-labeled DNA probe, followed by one or more washes in 2×SSC, 0.1% SDS at room temperature and one or more washes in 0.5×SSC, 0.1% SDS or 0.1×SSC, 0.1% SDS at 65-68° C. In particular, highly stringent conditions include, for example, 2 h to 4 days incubation at 42° C. using a DIG-labeled DNA probe (prepared by e.g. using a DIG labeling system; Roche Diagnostics GmbH, 68298 Mannheim, Germany) in a solution such as DigEasyHyb solution (Roche Diagnostics GmbH) with or without 100 μg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

A nucleic acid molecule of the present invention, such as for instance a nucleic acid molecule shown in SEQ ID NO:1 to 5 or a fragment or derivative thereof, may be isolated using standard molecular biology techniques and the sequence information provided herein. For example, using all or portion of the nucleic acid sequence shown in SEQ ID NO:1 to 5 as a hybridization probe, nucleic acid molecules according to the invention may be isolated using standard hybridization and cloning techniques (e.g., as described in Sambrook et al., supra).

Furthermore, oligonucleotides corresponding to or hybridizable to nucleotide sequences according to the invention may be prepared by standard synthetic techniques, e.g., using an automated DNA synthesizer.

The terms "homology" or "percent identity" are used interchangeably herein. For the purpose of this invention, it is defined here that in order to determine the percent identity of two nucleic acid sequences, the sequences are aligned for optimal comparison purposes (e.g., gaps may be introduced in the sequence of a first nucleic acid sequence for optimal alignment with a second nucleic acid sequence). The nucleotides at corresponding positions are then compared. When a position in the first sequence is occupied by the same nucleotide as the corresponding position in the second sequence, then the molecules are identical at that position. The percent identity between the two sequences is a function of the number of identical positions shared by the sequences [i.e., % identity=number of identical positions/total number of positions (i.e., overlapping positions)×100]. Preferably, the two sequences are the same length.

The skilled person will be aware of the fact that several different computer programs are available to determine the homology between two sequences. For instance, a comparison of sequences and determination of percent identity between two sequences may be accomplished using a mathematical algorithm. In a preferred embodiment, the percent identity between two amino acid sequences is determined using the Needleman and Wunsch (J. Mol. Biol. 48, 444-453, 1970) algorithm which has been incorporated into the GAP program in the GCG software package (available at http://www.accelrys.com), using either a Blossom 62 matrix or a PAM250 matrix, and a gap weight of 16, 14, 12, 10, 8, 6 or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at http://www.accelrys.com), using a NWSgapdna.CMP matrix and a gap weight of 40, 50, 60, 70 or 80 and a length weight of 1, 2, 3, 4, 5 or 6. In another embodiment, the percent identity between two nucleotide sequences is determined using the algorithm of E. Meyers and W. Miller (CABIOS, 4: 11-17, 1989) which has been incorporated into the ALIGN program (version 2.0) (available at http://vega.igh.cnrs.fr/bin/align-guess.cgi) using a PAM120 weight residue table, a gap length penalty of 12 and a gap penalty of 4.

The nucleic acid sequences, i.e. mRNA stabilizing elements, as of the present invention may be operatively linked to an appropriate promoter, which may be either a constitutive or inducible promoter. The promoter will be either the natural one or a promoter which is originally not naturally linked to the respective gene(s) involved in biosynthesis of a target fermentation product. The skilled person will know how to select suitable promoters. The expression constructs may contain sites for transcription initiation, termination, and, in the transcribed region, a ribosome binding site for translation. The coding portion of the mature transcripts expressed by the constructs may preferably include an initiation codon at the beginning and a termination codon appropriately positioned at the end of the polypeptide to be translated.

Promoters suitable for the expression of respective gene(s) involved in biosynthesis of a desired target fermentation product useful for the present invention can be found in the literature, see e.g. EP 405370, EP 635572, WO 01/21772, WO 04/106557, EP 950715 or WO 03/062409 for promoters used in the fermentative production of riboflavin, biotin, pantothenic acid, pyridoxine and enzymes selected from transferases or hydrolases, respectively.

A useful method for constructing a microorganism as of the present invention, i.e. introducing a stabilizing mRNA element downstream of the transcription start of a gene involved in production of a desired target fermentation product is shown in FIG. 1, wherein the gene(s) downstream of the promoter maybe any gene involved in biosynthesis of the desired target fermentation product, such as, e.g. panB, bioA, ribD, amyQ, wherein introduction of a herein disclosed mRNA stabilizing element leads to a more stable mRNA transcripts from the respective gene(s) which furthermore leads to increased yield and/or productivity of the respective target fermentation product. The sequences of said gene(s) involved in biosynthesis of the desired products are publicly available as known by the skilled person. Selection of recombinant microorganisms can be performed via introduction of an antibiotic resistance gene, such as for instance chloramphenicol, neomycin, streptomycin, spectinomycin or the like. Optionally, the natural promoter may furthermore replaced by a stronger such as e.g. the $P_{15}$ constitutive strong promoter.

As mentioned above, the nucleic acid sequences as of the present invention may be utilized in the genetic engineering of a suitable host cell to make it better and more efficient in the fermentation, for example in production of a target fermentation product as defined herein.

According to the invention a genetically engineered/recombinantly produced host cell (also referred to as recombinant cell or transformed cell) carrying such a mRNA stabilizing element as of the present invention such that the yield, production and/or efficiency of production of a target fermentation product, in particular vitamins or enzymes as defined herein, is improved. The host cell may be selected from a microorganism capable of producing said target fermentation product such as for instance vitamin B2, pantothenic acid, transferases or hydrolases from a given carbon source, in particular *Bacillus*, preferably *B. subtilis*.

A "transformed cell" or "recombinant cell" is a cell into which (or into an ancestor of which) has been introduced, by means of recombinant DNA techniques, a nucleic acid according to the invention leading to increased and/or enhanced stability of mRNA transcribed from the respective gene(s). Suitable host cells include cells of microorganisms capable of producing a given fermentation product, e.g., converting a given carbon source into a target product as defined above. Useful strains for performing said fermentation process are listed above and known in the art.

The present invention provides for a process for the production of a target fermentation product such as, e.g. riboflavin, biotin, pantothenic acid, folic acid, thiamin, pyridoxine, xylanase, amylase, protease, glucanase, amylomaltase or maltogenic amylase, wherein the production/yield of said target fermentation products using a recombinant organism is increased compared to a non-modified organism. As used herein, "improved yield of target fermentation product" means an increase of at least 5%, 10%, 25%, 30%, 40%, 50%, 75%, 100%, 200% or even more than 500%, compared to a wild-type microorganism, i.e. a non-modified microorganism.

Several substrates may be used as a carbon source in a process of the present invention, i.e. a process for production of a target fermentation product as mentioned above. Particularly suited carbon sources may be selected from compounds consisting of 3, 5 or 6 carbon atoms, such as e.g. D-glucose, glycerol, thick juice, dextrose, starch, sucrose or ribose. Preferably, the carbon source is D-glucose. The term "carbon source", "substrate" and "production substrate" in connection with the above process using a microorganism is used interchangeably herein.

A medium as used herein for the above process using a microorganism may be any suitable medium for the production of the desired target fermentation product. Typically, the medium is an aqueous medium comprising for instance salts, substrate(s), and a certain pH. The medium in which the substrate is converted into the desired product is also referred to as the production medium.

"Fermentation" or "production" or "fermentation process" as used herein may be the use of growing cells using media, conditions and procedures known to the skilled person, or the use of non-growing so-called resting cells, after they have been cultivated by using media, conditions and procedures known to the skilled person, under appropriate conditions for the conversion of suitable substrates into desired products such as e.g. vitamins or enzymes.

In one embodiment a microorganism is capable of the conversion of a certain substrate into the specified product by means of one or more biological conversion steps, without the need of any additional chemical conversion step. Said microorganism is cultured under conditions which allow such conversion from the substrate as defined above.

The produced target fermentation product may be recovered from the cells by any suitable means. Recovering means for instance that the produced fermentation product may be separated from the production medium. Optionally, the thus produced target fermentation product may be further processed.

In connection with the above process using a microorganism, in one aspect, the growing step can be performed in an aqueous medium, i.e. the growth medium, supplemented with appropriate nutrients for growth normally under aerobic conditions. The cultivation may be conducted, for instance, in batch, fed-batch, semi-continuous or continuous mode, wherein fed-batch or semi-continuous mode is preferred. The cultivation period may vary depending on for instance the host, target fermentation product, pH, temperature and nutrient medium to be used, and may be for instance about 10 h to about 10 days, preferably about 4 to about 7 days, more preferably about 2 to about 6 days, depending on the microorganism. If the microorganism is selected from bacteria, the cultivation may be conducted for instance at a pH of about 7.0, preferably in the range of about 6 to about 8, more preferably about 6.5 to 7.5. A suitable temperature range for carrying out the cultivation using bacteria may be for instance from about 13° C. to about 70° C., preferably from about 35° C. to about 39° C., more preferably from about 30° C. to about 39° C., and most preferably from about 36° C. to about 39° C. The culture medium for growth usually may contain such nutrients as assimilable carbon sources, e.g., D-glucose, glycerol, thick juice, dextrose, starch, sucrose or ribose; and digestible nitrogen sources such as organic substances, e.g., peptone, yeast extract and amino acids. The media may be with or without urea and/or corn steep liquor and/or baker's yeast. Various inorganic substances may also be used as nitrogen sources, e.g., nitrates and ammonium salts. Furthermore, the growth medium usually may contain inorganic salts, e.g., magnesium sulfate, manganese sulfate, potassium phosphate, and calcium carbonate. Cells obtained using the procedures described above can then be further incubated at essentially the same modes, temperature and pH conditions as described above, in the presence of substrates such as described above in such a way that they convert these substrates into the desired target fermentation product. Incubation can be done in a nitrogen-rich medium, containing, for example, organic nitrogen sources, e.g., peptone, yeast extract, baker's yeast, urea, amino acids, and corn steep liquor, or inorganic nitrogen sources, e.g., nitrates and ammonium salts, in which case cells will be able to further grow while producing the desired target fermentation product. Alternatively, incubation can be done in a nitrogen-poor medium, in which case cells will not grow substantially, and will be in a resting cell mode, or biotransformation mode. In all cases, the incubation medium may also contain inorganic salts, e.g., magnesium sulfate, manganese sulfate, potassium phosphate, and calcium chloride. An example of a suitable medium for production of a desired target fermentation product as described herein is described in WO 04/113510 (VF-medium), which is particularly useful with regards to *Bacillus*.

Analytical methods for determining the yield/productivity of a given target fermentation product are known in the art. Such methods may include, but are not limited to HPLC or use of indicator strains: for riboflavin, see e.g. Bretzel et al., J. Ind. Microbiol. Biotechnol. 22, 19-26, 1999; for biotin, see e.g. EP 635572 or Tanaka et al., J. Micro. Methods 6, 237-247, 1987; for pantothenic acid, see e.g. WO 04/113510; for folic acid, see e.g. Ullman's Encyclopedia of Industrial Chemistry, 7$^{th}$ Edition, 2007, Chapter Vitamins; for thiamin, see e.g. WO 04/106557; for pyridoxine, see e.g. Tazoe et al., Biosci. Biotechnol. Biochem. 63 (8), 1378-1382, 1999.

Methods for fermentation, isolation/purification and analytical methods with regards to target fermentation products selected from enzymes and which may be applicable for the present invention are disclosed in e.g. Rothstein et al., J. Bacteriol. 168 (2), 839-842, 1986 or Skolpap et al., Biotechnol. Bioeng. 86, 706-717, 2004 or Malhotra et al., Letters in Appl. Microbiol. 31, 378-384, 2000 (α-amylase from *B. licheniformis, B. subtilis* or *B. thermooleovorans*); Tang et al., Bioresource Technology 93, 175-181, 2004 (β-glucanase from *B. subtilis*); Heineken and O'Connor, J. Gen. Microbiol. 73, 35-44, 1972 or çalik et al., Biotechnol. Bioeng. 69, 301-311, 2000 (neutral protease from *B. subtilis* and *B. licheniformis*, respectively); Schneider et al., Can. J. Microbiol. 46, 784-789, 2000 or Mamo and, Appl. Biochem. Biotechnol. 87, 95-101, 2000 or Sindhu et al., Current Microbiol. 53, 167-172, 2006 (xylanase from e.g. *B. megaterium*).

The following examples are illustrative only and are not intended to limit the scope of the invention in any way.

BRIEF DESCRIPTION OF THE DRAWINGS

FIG. 1: the 3 different steps for constructing a genetically altered microorganism carrying an mRNA stabilizing element (St) downstream of a strong constitutive $P_{15}$ promoter via LFH-PCR are exemplified for the pantothenate (pan) operon comprising the genes panB, panC, panD (panBCD). For selection of recombinant microorganisms, the chloramphenicol (Cm) antibiotic resistance gene is used. For more explanation see the examples.

EXAMPLES

The following media as referred to in the examples are described in WO 04/106557: Tryptose Blood Agar Broth (TBAB) medium, Veal infusion-Yeast Extract broth (VY) medium, 10× Spizizen salts and Minimal Medium (MM).

100× Trace elements solution A: 12.5 g $MgCl_2.6H_2O$; 0.55 g $CaCl_2$; 1.35 g $FeCl_2.6H_2O$; 0.1 g $MnCl_2.4H_2O$; 0.17 g/l $ZnCl_2$; 0.043 g $CuCl_2.2H_2O$; 0.06 g $CoCl_2.6H_2O$; 0.06 g $Na_2MoO_4.2H_2O$; ad 1 l $H_2O$, autoclaved.

5× Minimal Salt Solution: 0.057 M $K_2SO_4$; 0.31 M $K_2HPO_4.5H_2O$; 0.22 M $KH_2PO_4$; 0.017 M Na-citrate.$7H_2O$; 0.004 M $MgSO_4$. $H_2O$, pH 7.0, autoclaved.

100× Trace elements solution B: 0.55 g $CaCl_2$; 0.17 g $ZnCl_2$; 0.043 g $CuCl_2.2H_2O$; 0.06 $CoCl_2.6H_2O$; 0.06 g $Na_2MoO_4.2H_2O$; ad 1 l $H_2O$, autoclaved.

Example 1

Integration of the aprE, grpE, cotG, SP82, RSBgsiB mRNA Stabilizing Element Downstream of the Native Promoter of the Riboflavin (Rib) Operon and the Native Strong Promoter of rpsD Protein overproduction mediated by the aprE, grpE, cotG, SP82 or RSBgsiB mRNA stabilizing element was tested via insertion of said mRNA stabilizing elements (SEQ ID NO:1 to 5) between the native rib operon promoter ($P_{rib}$) and the lacZ reporter gene in the first set of constructs. In a second set of constructs said mRNA stabilizing elements were inserted between the native strong rpsD promoter ($P_{rpsD}$ 1 and the lacZ reporter gene.

First, the pBest4 vector was constructed carrying the lacZ reporter gene and multiple cloning sites (MCS): The pBest-MCS+ (SEQ ID NO:21) and pBestMCS- (SEQ ID NO:22) oligonucleotides containing an AscI restriction site were annealed and cloned into the HindIII and BamHI digested pDG1728 plasmid (ECE114; Guerout-Fleury et al., 1996, *Gene* 180:57-61; available from BGSC). The resulting plasmid pBest4 was used to accommodate ten synthetic constructs at the 5'-end of the lacZ reporter gene, respectively.

In the first set of constructs with the native $P_{rib}$ promoter, the four synthetic DNA fragments contained (i) the rib promoter and the aprE stabilizing element ($P_{rib\Omega aprE}$; SEQ ID NO:23); (ii) the rib promoter and the grpE stabilizing element ($P_{rib\Omega grpE}$; SEQ ID NO:24); (iii) the rib promoter and the cotG stabilizing element ($P_{rib\Omega cotG}$; SEQ ID NO:25); and (iv) only the native rib promoter ($P_{rib}$; SEQ ID NO:26) used as a control.

In the second set of constructs with the native strong $P_{rpsD}$ promoter the six synthetic DNA fragments contained (i) the rpsD promoter and the aprE stabilizing element ($P_{rpsD\Omega aprE}$; SEQ ID NO:27); (ii) the rpsD promoter and the grpE stabilizing element ($P_{rpsD\Omega grpE}$; SEQ ID NO:28); (iii) the rpsD promoter and the cotG stabilizing element ($P_{rpsD\Omega cotG}$; SEQ ID NO:29); (iv) the rpsD promoter and the SP82 stabilizing element ($P_{rpsD\Omega sp82}$; SEQ ID NO:30); (v) the rpsD promoter and the RBSgsiB stabilizing element [RBSgsiB] ($P_{rpsD\Omega RBSgsiB}$; SEQ ID NO:31); and (vi) only the native rpsD promoter ($P_{rpsD}$; SEQ ID NO:32) used as a control. In the synthetic DNA constructs (see above) the mRNA stabilizing elements were inserted 10 nucleotides downstream of the +1 transcription start site.

The synthetic DNA fragments were synthesized and custom cloned by DNA2.0 Inc. (Menlo Park, Calif., USA). The synthetic DNA fragments shown in SEQ ID NOs: 23, 25, 27, 29 and 31 were inserted between the BamHI and SalI sites in pBest4 resulting in plasmids pBest55, pBest59, pBest70, pBest74, and pBest79, respectively. The synthetic DNA fragments shown in SEQ ID NOs: 26, 24, 32, 28 and 30 were inserted between the AscI and BamHI sites in pBest4 resulting in plasmids pBest51, pBest57, pBest66, pBest72, and pBest77, respectively. The ten plasmids were transformed into *B. subtilis* 1A747 [SPβ$^c$, prototroph, derivative of *B. subtilis* 168 (trpC2); available from BGSC] selecting for spectinomycin resistance (Spec$^r$) to integrate the different lacZ fusions into the amyE chromosomal locus, generating strains BE111 ($P_{rib}$-lacZ), BE115 ($P_{rib\Omega aprE}$-lacZ), BE117 ($P_{rib\Omega grpE}$-lacZ), BE119 ($P_{rib\Omega cotG}$-lacZ), BE126 ($P_{rpsD}$-lacZ), BE130 ($P_{rpsD\Omega aprE}$-lacZ), BE132 ($P_{rpsD\Omega grpE}$-lacZ), BE134 ($P_{rpsD\Omega cotG}$-lacZ), BE137 ($P_{rpsD\Omega SP82}$-lacZ) and BE139 ($P_{rpsD\Omega RBSgsiB}$-lacZ). The correct double cross-over integration was confirmed with the α-amylase assays (Prágai et al., 2001, *J. Bacteriology* 183:2505-2515): transformants with the derivatives of pBest4 plasmid were streaked onto TBAB agar (WO 04/106557) containing 1% starch (Sigma) for the test of the production of α-amylase. After 24 h of incubation at 37° C. the halos produced as a result of starch hydrolysis were visualized with staining using Lugol (iodine/potassium iodide) solution (Sigma). After double cross-over recombination of the pBest4 derivatives into the amyE gene of the *B. subtilis* 1A747 chromosome, no halo was formed around the two BE strains carrying the different lacZ fusions and spec gene in the amyE gene colonies of the Spec$^r$ transformants.

Determination of β-galactosidase activities were performed as follows: *B. subtilis* BE strains were inoculated in LB rich medium containing 100 µg/ml Spec and in BFA defined minimal medium containing 100 µg/ml Spec and grown overnight at 37° C. with an agitation of 250 rpm. Overnight cultures were diluted 100-fold in fresh LB medium (25 g LB broth, Merck, Catalog #1.10285.0500 ad 1 l $H_2O$, autoclaved) and in fresh BFA defined minimal medium (1× Minimal Salt Solution, supra; 1× Trace elements solution B, supra; 0.4% glucose; 0.2% L-glutamine; 4 mg $FeCl_3$; 0.2 mg $MnSO_4$, ad 1 l $H_2O$) and grown at 37° C. with an agitation of 250 rpm. Samples were collected hourly for determination of optical density at 600 nm ($OD_{600}$) and β-galactosidase activity (cell pellet from 0.1-1 ml of culture). The β-galactosidase samples were stored at −20° C. The β-galactosidase assay was performed and the specific β-galactosidase activity (expressed in nmol ONP/min/$OD_{600}$; ONP is 2-nitrophenol) was determined as described previously (Prágai and Harwood, 2002, *Microbiology* 148:1593-1602). As a result, BE115 strain produced 4-5-fold more specific β-galactosidase activity, BE117 produced 2-2.5-fold more specific β-galactosidase activity and BE119 produced 2-2.5-fold more specific β-galactosidase activity than the isogenic strain BE111 (P$_{rib}$-lacZ) without the mRNA stabilizing elements in both tested media. When using the rpsD promoter strains the results were as follows: BE132 strain produced 2.5-3-fold more specific β-galactosidase activity, BE134 produced 2-2.5-fold more specific β-galactosidase activity, BE137 produced 1.5-2-fold more specific β-galactosidase activity and BE139 produced 17-18-fold more specific β-galactosidase activity than the isogenic strain BE126 (P$_{rpsD}$-lacZ) without the mRNA stabilizing elements in both tested media.

Example 2

Production of Riboflavin Via Deregulation and Use of the mRNA Stabilizing Elements To analyze the effect of the mRNA stabilizing elements on riboflavin production in *Bacillus subtilis*, three mRNA stabilizing elements, i.e. SEQ ID NO:1, 2 and 5 were inserted upstream of the rib operon. Six strains were constructed carrying (i) the wild-type P$_{rib}$ promoter [control], (ii) the P$_{15}$ constitutive strong promoter [deregulation], (iii) the P$_{rpsD}$ constitutive strong promoter [deregulation], (iv) the P$_{15}$ constitutive strong promoter and the aprE mRNA stabilizing element [deregulation and mRNA stabilization], (v) the P$_{15}$ constitutive strong promoter and the grpE mRNA stabilizing element [deregulation and mRNA stabilization], and (vi) the P$_{rpsD}$ constitutive strong promoter and the RBSgsiB mRNA stabilizing element [deregulation and mRNA stabilization]. The P$_{15}$ promoter (also named as PE4 promoter) of the *B. subtilis* bacteriophage SPO1 (Steward et al., 1998, Virology, 246:329-340) was obtained from plasmid pXI23roDTD-SPOT-15, a derivative of plasmid pX12 (Hümbelin et al., 1999, *J. Ind. Microbiol. Biotech.* 22:1-7). The P$_{rpsD}$ promoter was obtained from the chromosomal DNA of *B. subtilis* 1A747 (Grundy and Henkin, 1990, J. Bacteriol. 172:6372-6379; Grundy and Henkin, 1990, J. Bacteriol. 173:4595-4602; Grundy and Henkin, 1992, J. Bacteriol. 174:6763-6770).

For replacing the native P$_{rib}$ promoter with constitutive strong promoters (P$_{15}$ and P$_{rpsD}$) and inserting the mRNA stabilizing elements (aprE, grpE and RBSgsiB) upstream of the five rib genes, first, the riboflavin-auxotroph *B. subtilis* BS3813 strain was constructed. In BS3813, the promoter of the riboflavin operon, the 5' untranslated sequence and the 5' end of the ribD structural gene was replaced by a neomycin resistance (neo) cassette obtained from plasmid pBEST501 (Itaya et al., 1989, Nucleic Acid Res. 17:4410). For the strain construction, Long Flanking Homology Polymerase Chain Reaction (LFH-PCR) was used to generate DNA fragments containing the 1236-bp neo resistance flanked by the 526-bp upstream region of the native P$_{rib}$ promoter (flank 5') and the 512-bp 3' end of ribD gene (flank 3'). Therefore, three DNA fragments flank 5', the neo gene and flank 3' were first PCR amplified. DNA fragments flank 3' and flank 5' were generated as follows: 0.2 µl of a 100 mM solution of primers p50 (SEQ ID NO:33) together with p51 (SEQ ID NO:34) or primers p44 (SEQ ID NO:35) together with p45 (SEQ ID NO:36) were added to 0.1 µg *B. subtilis* 1A747 chromosomal DNA in a 50 µl reaction volume containing 1 µl of 40 mM dNTP's, 5 µl of 10× buffer and 0.5 µl Pfu polymerase enzyme (Stratagene). For generating DNA fragment containing the neo gene, 0.2 µl of a 100 mM solution of primers p9 (SEQ ID NO:37) together with p10 (SEQ ID NO:38) were added to 0.05 µg pBEST501 DNA containing the neo resistance cassette in a 50 µl reaction volume containing 1 µl of 40 mM dNTP's, 5 µl of 10× buffer and 0.5 µl Pfu polymerase enzyme (Stratagene). The PCR reactions were performed in 30 cycles of three sequential steps: (i) denaturing step at 95° C. for 30 sec; (ii) annealing step at 52° C. for 30 sec; (iii) elongation step at 72° C. for 1.5 min. The three PCR products were separated by agarose gel electrophoresis and extracted from the gel using the MinElute Gel Extraction Kit (Qiagen). In the final LFH-PCR reaction, the three purified PCR products (flank 5', neo gene and flank 3') were assembled: 0.2 µl of a 100 mM solution of primers p45 together with p51, 0.5 µl flank 5' PCR product (25 ng), 0.5 µl flank 3' PCR product (25 ng) and 2 µl neo resistance cassette (100 ng) were added in a final 50 µl reaction volume containing 1 µl of 40 mM dNTP's, 5 µl of 10× buffer and 0.5 µl HF Expand polymerase enzyme (Roche Biochemicals). The LFH-PCR reaction was performed in 35 cycles of three sequential steps: (i) denaturing step at 95° C. for 30 sec; (ii) annealing step at 52° C. for 30 sec; (iii) elongation step at 72° C. for 2.5 min. The assembled LFH-PCR product was purified by using the QiaQuick PCR purification kit (Qiagen). The purified LFH-PCR product (2 µg) was used for transformation of *B. subtilis* 1 A747 competent cells. Neomycin-resistant (Nm$^r$) transformants were selected on TBAB plates containing 2 mg/L neomycin (Nm) and 100 mg/L riboflavin. The correct genotype of the resulting riboflavin-auxotroph and Nm$^r$ BS3813 strain was confirmed by two PCR reactions using primers p45 together with p10, and primers p51 together with p9, and chromosomal DNA of the transformants as template DNA. The PCR reactions were performed using standard reaction conditions as described above for the generation of DNA fragments containing flank 5' and flank 3'. In addition, the sequence of the 3' end of ribD in BS3813 was confirmed by sequencing.

In the second strain construction step, the neo gene of the riboflavin-auxotroph *B. subtilis* BS3813 strain was replaced using five LFH-PCR products containing (i) the P$_{15}$ constitutive strong promoter (P$_{15}$); (ii) the P$_{rpsD}$ constitutive strong promoter (P$_{rpsD}$), (iii) the P$_{15}$ constitutive strong promoter and the grpE mRNA stabilizing element (P$_{15\Omega aprE}$), (iv) the P$_{15}$ constitutive strong promoter and the grpE mRNA stabilizing element (P$_{15\Omega grpE}$), and (v) the P$_{rpsD}$ constitutive strong promoter and the RBSgsiB mRNA stabilizing element (P$_{rpsD\Omega RBSgsiB}$) upstream of the rib operon.

For the construction of the LFH-PCR product containing the P$_{15}$ribDEAHT construct two standard PCR reactions were performed in which the sequence of the P$_{15}$ promoter was introduced into the PCR products. In a third PCR reaction the two PCR products were combined. For amplifying PCR product 1 containing the 5' region of the riboflavin operon and the 5'-end of the P$_{15}$ promoter, the primer pair p45 and p63 (SEQ ID NO:40) and the chromosomal DNA from strain *B. subtilis* 1A747 as template was used under standard PCR conditions. For amplifying PCR product 2 containing the ribD at the 3'-end of the P$_{15}$ promoter, primers p51 and Spo15S' (SEQ ID NO:39) and the chromosomal DNA from strain *B. subtilis* 1 A747 as template was used under standard PCR conditions. In the standard LFH-PCR reaction, the gel-purified PCR products 1 and 2 were assembled into one DNA fragment using primer pair p45 and p51 as described before. The purified LFH-PCR product was transformed into the riboflavin-auxotroph *B. subtilis* BS3813 competent cells, in which the riboflavin promoter region and the 5' part of ribD was replaced with the neo resistance cassette. Riboflavin-prototroph transformants were selected on minimal agar medium (SMM: 886 ml 1.5% agar in distilled H$_2$O; autoclaved for 30 min at 121° C. followed by addition of 100 ml 10× Spizizen salts, supra, 4 ml 50% glucose, 10 ml 100× Trace elements solution A, supra). The riboflavin-prototroph Bacillus transformants were suspended in 1 ml 0.9% NaCl solution and 100 µL the 500-fold dilution of the original cell suspension was plated on TBAB agar plate. Single colonies were transferred onto fresh TBAB agar plates and TBAB agar plates supplemented with 2 mg/L Nm and 100 mg/L riboflavin. The correct transformants grew only on TBAB agar plate and therefore they were neomycin-sensitive. In addition, the genotype was confirmed with sequencing of the ribD region. The final strain was called BS3944 (P$_{15}$ribDEAHT).

For the construction of the LFH-PCR product containing the P$_{15\Omega aprE}$ construct, two standard PCR reactions were performed in which the DNA sequence of the aprE mRNA stabilizing element was integrated into two PCR products. For amplifying PCR product 1 containing the 5' region of the riboflavin operon and the P$_{15}$ promoter at the 5'-end of the aprE mRNA stabilizing element, the primers p45 together with p143' (SEQ ID NO:41) and the chromosomal DNA from strain BS3944 as template was used under standard PCR conditions. For amplifying PCR product 2 containing the ribD at the 3'-end of the aprE mRNA stabilizing element, the primers p51 together with p142 (SEQ ID NO:42) and the chromosomal DNA from strain BS3944 as template were used under standard PCR conditions. In the standard LFH-PCR reaction, the gel-purified PCR products 1 and 2 were assembled into one DNA fragment using primer pair p45 and p51 as described before. The purified LFH-PCR product was transformed again into the riboflavin-auxotroph B. subtilis BS3813 competent cells, in which the riboflavin promoter region and the 5' part of ribD was replaced with the neo resistance gene. Riboflavin-prototroph Bacillus transformants were selected on SMM plates. Transformants were suspended in 1 ml 0.9% NaCl solution and 100 µL the 500-fold dilution of the original cell suspension is plated on TBAB agar plate. Single colonies were transferred onto fresh TBAB agar plates and TBAB agar plates supplemented with 2 mg/L Nm and 100 mg/L riboflavin. The correct transformants grew only on TBAB agar plate and therefore they were neomycin-sensitive. In addition, the genotype was confirmed with sequencing of the ribD region. The resulting strain was BS5193 (P$_{15\Omega aprE}$ribDEAHT).

The same method was applied for inserting the grpE mRNA stabilizing element between the P$_{15}$ promoter and the rib operon resulting in strain BS5196 (P$_{15\Omega grpE}$ribDEAHT), wherein for the first two PCR reactions primer pairs p45 and p145' (SEQ ID NO:43) and p51 and p144 (SEQ ID NO:44) were used together with the chromosomal DNA from strain BS3944 as template.

For the construction of the LFH-PCR product containing the P$_{rpsD}$ribDEAHT construct three DNA fragments were PCR amplified containing the P$_{rpsD}$ promoter (PST2 fragment) flanked by the 1013-bp upstream region of the rib operon (flank 5') and the 1108-bp ribD gene (flank 3'). DNA fragments flank 5' and flank 3' were generated with standard PCR reactions as described before using primer pair PUS1 (SEQ ID NO:45) and PSTP2 (SEQ ID NO:46) and primer pair PST2P3 (SEQ ID NO:47) and p51 together with B. subtilis 1A747 chromosomal DNA as template. For generating PST2 DNA fragment primers PSTF (SEQ ID NO:48) and PSTR2 (SEQ ID NO:49) and B. subtilis BE126 chromosomal DNA as template was used. After gel extraction the three PCR products were assembled into an LFH-PCR product as described before using primers PUS1 and p51. The purified LFH-PCR product was transformed into the riboflavin-auxotroph B. subtilis BS3813 competent cells. Riboflavin-prototroph and Nm sensitive transformants were selected on minimal agar medium as described before and the genotype was confirmed with sequencing of the ribD region. The final strain was called BE460 (P$_{rpsD}$ribDEAHT).

The same method was applied for inserting the RBSgsiB mRNA stabilizing element between the P$_{rpsD}$ promoter and the rib operon resulting in strain BE454 (P$_{rpsD\Omega RBSgsiB}$ribDEAHT). For the construction of the LFH-PCR product three DNA fragments were generated: the 162-bp PST1 fragment containing the P$_{rpsD}$ promoter and RBSgsiB stabilizing element and flanked by the 1013-bp upstream region of the rib operon (flank 5') and the 1108-bp ribD gene (flank 3'). DNA fragments flank 5' and flank 3' were generated with standard PCR reactions as described before using primer pair PUS1 and PSTP2 and primer pair PST1P3 (SEQ ID NO:50) and p51 together with B. subtilis 1A747 chromosomal DNA as template. For generating PST1 DNA fragment primers PSTF and PSTR1 (SEQ ID NO:51) and B. subtilis BE139 chromosomal DNA as template was used.

In order to transfer the new constructs into a riboflavin producing background, PBS1 phage lysates from BS3944, BS5193, BS5196, BE460 and BE454 were prepared as described in Cutting and Vander Horn, 1990, Genetic Analysis in Harwood and Cutting (eds), Molecular biological methods for Bacillus. New York: John Wiley and Sons. Generalized transduction mediated by PBS1 phage was used to transfer the five constructs P$_{15}$ribDEAHT, P$_{15\Omega aprE}$ribDEAHT, P$_{15\Omega grpE}$ribDEAHT, P$_{rpsD}$ribDEAHT and P$_{rpsD\Omega RBSgsiB}$ribDEAHT into BS5178 (ΔribD::neo tktR357A, ribC, spo0A12). BS5178 is riboflavin-auxotroph since the promoter of the riboflavin operon, the 5' untranslated sequence and the 5' end of ribD structural gene was replaced by a neo resistance cassette similarly as it was described above for BS3813. After the PBS1 mediated transduction of BS5178, riboflavin-prototroph and Nm sensitive strains were selected on SMM plates as described before. The resulting strains were BS5240 (P$_{15}$ribDEAHT), BS5237 (P$_{15\Omega aprE}$ribDEAHT), BS5238 (P$_{15\Omega grpE}$ribDEAHT), BE476 (P$_{rpsD}$ribDEAHT) and BE475 (P$_{rpsD\Omega RBSgsiB}$ribDEAHT). The isogenic control strain with the wild-type rib operon was BS5191 (P$_{rib}$ribDEAHT). The six strains BS5191, BS5240, BS5137, BS5138, BE476 and BE475 were evaluated for riboflavin production in shake flask cultures: strains were inoculated from frozen glycerol stocks in 5 ml VY rich medium (WO 04/106557) and grown overnight at 37° C. with an agitation of 280 rpm. Cells were collected by centrifugation and re-suspended in 1 ml riboflavin screening medium (RSM: 100 ml 10× Spizizen salts, supra; 10 ml 100× Trace elements solution A, supra, 2 ml 50% glucose; 36 ml 25% raffinose 10 ml 10% yeast extract, ad 1 l H$_2$O). 250 µl of the cell suspension was used for inoculation of 25 ml RSM in 250 mL baffled shake flasks. After 48 h incubation at 39° C. with an agitation of 220 rpm, 500 µl culture were taken and 35 µl 4 N NaOH was mixed with the sample for 1 minute at room temperature allowing to dissolve the riboflavin crystals. Samples were neutralized by the addition of 465 µl 1 M potassium phosphate buffer (pH 6.8) and purified with centrifugation (5 min, 13.2 krpm). The supernatant was used for HPLC determination of the concentrations of riboflavin and two side products: 6,7-dimethyl-8-ribityllumazine (DMRL) and oxolumazine. In addition, a second culture sample was taken and after centrifugation (5 min, 13.2 krpm) the supernatant was used for determination of the concentrations of the residual glucose and raffinose in the medium.

HPLC analysis for riboflavin analysis was performed as follows: samples from shake flask cultures were analyzed by HPLC using an Agilent 1100 HPLC system equipped with a thermostatted autosampler, a diode array and a fluorescence detector. The separation was performed on a Supelcosil LC-8 DB-5µ column (150 mm×4.6 mm) equipped with a 4 mm LC-8 DB guard column. A mixture of 0.1 M acetic acid and methanol was used as mobile phase. Gradient elution was applied starting at 2% methanol (constant for 5 min) and going up to 50% methanol in 15 minutes. The column was kept at 20° C. The signal was recorded by UV at 280 nm. Riboflavin was well separated from the impurities (e.g. side products: DMRL and oxolumazine) and eluted at 15.2 minutes. The calibration was based on reference material obtained from Fluka. The calibration range of the method was from 10 µg/ml to 1 mg/ml. For HPLC analysis of the sugars, the following procedure was applied using an Agilent 1100 series HPLC system with a quaternary pump, an autosampler a UV- and a refractive index detector. The separation was achieved on a CAPCELL PAK NH2 UG80 column (4.6 mm×250 mm, 5µ) (Shiseido). The optimal column temperature was 35° C. The mobile phase was a mixture of acetonitrile and DI water at a 65/35 ratio. The flow rate was 1.0 ml/min and the injection volume set to 5 µl. The refractive index signal was monitored and used for detection. The calibration range for each compound was from 0.5 mg/ml to 30 mg/ml.

The results showed that increasing the transcription level of the ribDEAHT operon by the constitutive strong $P_{15}$ promoter and deleting the regulatory riboswitch sequence [deregulation] resulted in 2.3-fold higher riboflavin yield on carbon source for BS5240 than obtained with the control strain BS5191 containing the wild-type rib operon. Using the constitutive strong $P_{15}$ promoter and increasing the stability of the ribDEAHT transcripts by the aprE and grpE mRNA stabilizing element [deregulation and mRNA stabilization], respectively led to a 3.9-fold and 6.4-fold higher riboflavin yield on carbon source for BS5237 and BS5238, respectively than it was produced by the control strain BS5191. Using $P_{rpsD}$ and increasing the stability of the ribDEAHT transcripts by introducing the RBSgsiB mRNA stabilizing element [deregulation and mRNA stabilization] led to a 1.5-fold higher riboflavin yield on carbon source for BE475 than it was produced by the control strain BE476 ($P_{rpsD}$ribDEAHT) [deregulation]. Thus, mRNA stabilization resulted in an additional increase of at least 50% in the riboflavin yield. A comparison between the amount of riboflavin produced from the control strain BS5191 containing the wild-type rib operon and a strain containing the natural $P_{rib}$ together with the respective mRNA stabilizing elements shows an increase of at least 10% when using the mRNA stabilizing elements. The results show that mRNA stabilization is a powerful tool for strain engineering and it enhances significantly the increase of riboflavin yield resulted both using the natural promoter as well as by the deregulation of the rib operon with the constitutive strong SPO1 promoter $P_{15}$.

Example 3

Integration of the mRNA Stabilizing Elements Downstream of the Genes Involved in Biotin, Pantothenic Acid and α-Amylase The mRNA stabilizing elements can be used to increase the yield of a target fermentation product other than riboflavin, such as e.g. biotin, pantothenic acid or α-amylase. Construction of genetically engineered B. subtilis strains carrying the respective mRNA stabilizing elements downstream of either the natural promoter or a strong constitutive promoter such as e.g. $P_{15}$ is performed according to Example 2 or FIG. 1.

For increasing the yield of biotin, the steps described in FIG. 1 are followed, wherein the mRNA stabilizing elements are introduced between the natural or the constitutive promoter and the bioA gene. The primers for the PCR reactions are constructed based on the publicly available sequences, including the sequence for bioA.

For increasing the yield of pantothenate, the steps described in FIG. 1 are exactly followed, wherein the mRNA stabilizing elements are introduced between the natural or the constitutive promoter and the panB gene. The primers for the PCR reactions are constructed based on the publicly available sequences, including the sequence for panB.

The amount of the respective target fermentation product is increased by at least 10% when using the natural promoter and at least 50% when using the strong constitutive promoter.

The invention claimed is:

1. A process for improving or increasing the production of a target fermentation product by a microorganism of the genus *Bacillus*, wherein the target fermentation product is selected from the group consisting of riboflavin, biotin, thiamin, pantothenate and vitamin B6 (pyridoxine), wherein said microorganism is incubated in a aqueous medium comprising a carbon source, and wherein the target fermentation product is isolated as the fermentation product, and wherein said microorganism is genetically altered by introducing downstream of a gene involved in the biosynthetic pathway of said target fermentation product a polynucleotide selected from the group consisting of: (a) a polynucleotide comprising the nucleotide sequence of SEQ ID NO:2; and (b) a polynucleotide which has at least 95% sequence identity to the polynucleotide of SEQ ID NO:2 and has mRNA-stabilizing activity.

2. The process according to claim 1, wherein the microorganism is *Bacillus subtilis*.

3. The process according to claim 1, wherein the target fermentation product is riboflavin.

4. The process according to claim 3, wherein the yield of riboflavin is improved by at least 5% compared to production using a non-modified microorganism.

* * * * *

SEQUENCE LISTING

<160> NUMBER OF SEQ ID NOS: 51

<210> SEQ ID NO 1
<211> LENGTH: 41
<212> TYPE: DNA
<213> ORGANISM: Bacillus subtilis

<400> SEQUENCE: 1
acagaatagt cttttaagta agtctactct gaattttttt a                41

<210> SEQ ID NO 2
<211> LENGTH: 57
<212> TYPE: DNA
<213> ORGANISM: Bacillus subtilis

<400> SEQUENCE: 2
attttatcga agggcagcac ctgtccttct ccttacactt tgagggaggt gaacaca    57

<210> SEQ ID NO 3
<211> LENGTH: 27

```
<212> TYPE: DNA
<213> ORGANISM: Bacillus subtilis

<400> SEQUENCE: 3
aaggatcttc atccttaaca tattttt                                          27

<210> SEQ ID NO 4
<211> LENGTH: 42
<212> TYPE: DNA
<213> ORGANISM: Bacteriophage SP82

<400> SEQUENCE: 4
ggagccgctg agctaccaca gattgtgaaa ggagaggtta ac                         42

<210> SEQ ID NO 5
<211> LENGTH: 19
<212> TYPE: DNA
<213> ORGANISM: Bacillus subtilis

<400> SEQUENCE: 5
aaaggaggaa ttcaaaatg                                                   19

<210> SEQ ID NO 6
<211> LENGTH: 18
<212> TYPE: DNA
<213> ORGANISM: Artificial Sequence
<220> FEATURE:
<223> OTHER INFORMATION: synthetic primer

<400> SEQUENCE: 6
acagaatagt cttttaag                                                    18

<210> SEQ ID NO 7
<211> LENGTH: 18
<212> TYPE: DNA
<213> ORGANISM: Artificial Sequence
<220> FEATURE:
<223> OTHER INFORMATION: synthetic primer

<400> SEQUENCE: 7
taaaaaaatt cagagtag                                                    18

<210> SEQ ID NO 8
<211> LENGTH: 18
<212> TYPE: DNA
<213> ORGANISM: Artificial Sequence
<220> FEATURE:
<223> OTHER INFORMATION: synthetic primer

<400> SEQUENCE: 8
attttatcga agggcagc                                                    18

<210> SEQ ID NO 9
<211> LENGTH: 18
<212> TYPE: DNA
<213> ORGANISM: Artificial Sequence
<220> FEATURE:
<223> OTHER INFORMATION: synthetic primer

<400> SEQUENCE: 9
tgtgttcacc tccctcaa                                                    18

<210> SEQ ID NO 10
<211> LENGTH: 18
<212> TYPE: DNA
<213> ORGANISM: Artificial Sequence
```

-continued

```
<220> FEATURE:
<223> OTHER INFORMATION: synthetic primer

<400> SEQUENCE: 10
aaggatcttc atccttaa                                                 18

<210> SEQ ID NO 11
<211> LENGTH: 18
<212> TYPE: DNA
<213> ORGANISM: Artificial Sequence
<220> FEATURE:
<223> OTHER INFORMATION: synthetic primer

<400> SEQUENCE: 11
aaaaatatgt taaggatg                                                 18

<210> SEQ ID NO 12
<211> LENGTH: 18
<212> TYPE: DNA
<213> ORGANISM: Artificial Sequence
<220> FEATURE:
<223> OTHER INFORMATION: synthetic primer

<400> SEQUENCE: 12
ggagccgctg agctacca                                                 18

<210> SEQ ID NO 13
<211> LENGTH: 18
<212> TYPE: DNA
<213> ORGANISM: Artificial Sequence
<220> FEATURE:
<223> OTHER INFORMATION: synthetic primer

<400> SEQUENCE: 13
gttaacctct cctttcac                                                 18

<210> SEQ ID NO 14
<211> LENGTH: 18
<212> TYPE: DNA
<213> ORGANISM: Artificial Sequence
<220> FEATURE:
<223> OTHER INFORMATION: synthetic primer

<400> SEQUENCE: 14
aaaggaggaa ttcaaaat                                                 18

<210> SEQ ID NO 15
<211> LENGTH: 18
<212> TYPE: DNA
<213> ORGANISM: Artificial Sequence
<220> FEATURE:
<223> OTHER INFORMATION: synthetic primer

<400> SEQUENCE: 15
cattttgaat tcctcctt                                                 18

<210> SEQ ID NO 16
<211> LENGTH: 30
<212> TYPE: DNA
<213> ORGANISM: Bacillus subtilis

<400> SEQUENCE: 16
cagaatagtc ttttaagtaa gtctactctg                                    30

<210> SEQ ID NO 17
<211> LENGTH: 51
```

```
<212> TYPE: DNA
<213> ORGANISM: Bacillus subtilis

<400> SEQUENCE: 17
tttatcgaag ggcagcacct gtccttctcc ttacactttg agggaggtga a        51

<210> SEQ ID NO 18
<211> LENGTH: 16
<212> TYPE: DNA
<213> ORGANISM: Bacillus subtilis

<400> SEQUENCE: 18
aaggatcttc atcctt                                              16

<210> SEQ ID NO 19
<211> LENGTH: 17
<212> TYPE: DNA
<213> ORGANISM: Bacteriophage SP82

<400> SEQUENCE: 19
ggagccgctg agctacc                                             17

<210> SEQ ID NO 20
<211> LENGTH: 8
<212> TYPE: DNA
<213> ORGANISM: Bacillus subtilis

<400> SEQUENCE: 20 aaaggagg                                                        8

<210> SEQ ID NO 21
<211> LENGTH: 52
<212> TYPE: DNA
<213> ORGANISM: Artificial Sequence
<220> FEATURE:
<223> OTHER INFORMATION: synthetic primer

<400> SEQUENCE: 21
gatccggcgc gccggccggc cgtttaaacg cggccgcgca tgccctgcag ga       52

<210> SEQ ID NO 22
<211> LENGTH: 52
<212> TYPE: DNA
<213> ORGANISM: Artificial Sequence
<220> FEATURE:
<223> OTHER INFORMATION: synthetic primer

<400> SEQUENCE: 22
agcttcctgc agggcatgcg cggccgcgtt taaacggccg gccggcgcgc cg       52

<210> SEQ ID NO 23
<211> LENGTH: 146
<212> TYPE: DNA
<213> ORGANISM: Bacillus subtilis

<400> SEQUENCE: 23
ctcaaattgt aagtttattt cattgcgtac tttaaaaagg atcgctataa taaccaataa    60
ggacacagaa tagtctttta agtaagtcta ctctgaattt ttttaggtgg tgaactactg   120
tggaagttac tgacgtaaga ttacgg                                       146

<210> SEQ ID NO 24
<211> LENGTH: 122
<212> TYPE: DNA
<213> ORGANISM: Bacillus subtilis
```

<400> SEQUENCE: 24
ctcaaattgt aagtttattt cattgcgtac tttaaaaagg atcgctataa taaccaataa      60
ggacaatttt atcgaagggc agcacctgtc cttctcctta cactttgagg gaggtgaaca     120
ca                                                                    122

<210> SEQ ID NO 25
<211> LENGTH: 133
<212> TYPE: DNA
<213> ORGANISM: Bacillus subtilis

<400> SEQUENCE: 25
ctcaaattgt aagtttattt cattgcgtac tttaaaaagg atcgctataa taaccaataa      60
ggacaaagga tcttcatcct taacatattt ttggtggtga actactgtgg aagttactga    120
cgtaagatta cgg                                                        133

<210> SEQ ID NO 26
<211> LENGTH: 65
<212> TYPE: DNA
<213> ORGANISM: Bacillus subtilis

<400> SEQUENCE: 26
ctcaaattgt aagtttattt cattgcgtac tttaaaaagg atcgctataa taaccaataa      60
ggaca                                                                  65

<210> SEQ ID NO 27
<211> LENGTH: 224
<212> TYPE: DNA
<213> ORGANISM: Bacillus subtilis

<400> SEQUENCE: 27
gatctttagt tgttctacc atgtttttat cacctaaaag tttaccacta attttgttt       60 attatatcat aaacggtgaa gcaataatgg aggaatggtt gacttcaaaa caaataaatt    120
atataatgac ctttgtgtga aatcagaata gtcttttaag taagtctact ctgaattttt    180
ttaggtggtg aactactgtg gaagttactg acgtaagatt acgg                     224

<210> SEQ ID NO 28
<211> LENGTH: 200
<212> TYPE: DNA
<213> ORGANISM: Bacillus subtilis

<400> SEQUENCE: 28
gatctttagt tgttctacc atgtttttat cacctaaaag tttaccacta attttgttt       60 attatatcat aaacggtgaa gcaataatgg aggaatggtt gacttcaaaa caaataaatt    120
atataatgac ctttgtgtga aatattttat cgaagggcag cacctgtcct tctccttaca    180
ctttgaggga ggtgaacaca                                                 200

<210> SEQ ID NO 29
<211> LENGTH: 211
<212> TYPE: DNA
<213> ORGANISM: Bacillus subtilis

<400> SEQUENCE: 29
gatctttagt tgttctacc atgtttttat cacctaaaag tttaccacta attttgttt       60 attatatcat aaacggtgaa gcaataatgg aggaatggtt gacttcaaaa caaataaatt    120
atataatgac ctttgtgtga aataaggatc ttcatcctta acatattttt ggtggtgaac    180

```
tactgtggaa gttactgacg taagattacg g                                     211

<210> SEQ ID NO 30
<211> LENGTH: 185
<212> TYPE: DNA
<213> ORGANISM: Bacillus subtilis

<400> SEQUENCE: 30
gatctttagt ttgttctacc atgttttat cacctaaaag tttaccacta attttgttt        60 attatatcat aaacggtgaa gcaataatgg aggaatggtt gacttcaaaa caaataaatt      120
atataatgac ctttgtgtga aatggagccg ctgagctacc acagattgtg aaaggagagg      180
ttaac                                                                  185

<210> SEQ ID NO 31
<211> LENGTH: 186
<212> TYPE: DNA
<213> ORGANISM: Bacillus subtilis

<400> SEQUENCE: 31
gatctttagt ttgttctacc atgttttat cacctaaaag tttaccacta attttgttt        60 attatatcat aaacggtgaa gcaataatgg aggaatggtt gacttcaaaa caaataaatt      120
atataatgac ctttgtgtga ataaaggag gaattcaaaa tggaagttac tgacgtaaga      180
ttacgg                                                                 186

<210> SEQ ID NO 32
<211> LENGTH: 143
<212> TYPE: DNA
<213> ORGANISM: Bacillus subtilis

<400> SEQUENCE: 32
gatctttagt ttgttctacc atgttttat cacctaaaag tttaccacta attttgttt        60 attatatcat aaacggtgaa gcaataatgg aggaatggtt gacttcaaaa caaataaatt      120
atataatgac ctttgtgtga aat                                              143

<210> SEQ ID NO 33
<211> LENGTH: 47
<212> TYPE: DNA
<213> ORGANISM: Artificial Sequence
<220> FEATURE:
<223> OTHER INFORMATION: synthetic primer

<400> SEQUENCE: 33
gtgtcaaaac gcataccatt ttgaacgagt tggcacagtg aaagccg                    47

<210> SEQ ID NO 34
<211> LENGTH: 23
<212> TYPE: DNA
<213> ORGANISM: Artificial Sequence
<220> FEATURE:
<223> OTHER INFORMATION: synthetic primer

<400> SEQUENCE: 34
ctattccttt gtcggttttg ccg                                              23

<210> SEQ ID NO 35
<211> LENGTH: 49
<212> TYPE: DNA
<213> ORGANISM: Artificial Sequence
<220> FEATURE:
<223> OTHER INFORMATION: synthetic primer
```

```
<400> SEQUENCE: 35
gatctcgacc tgcagcccaa gcgaaataaa cttacaattt gagaaaaac            49

<210> SEQ ID NO 36
<211> LENGTH: 21
<212> TYPE: DNA
<213> ORGANISM: Artificial Sequence
<220> FEATURE:
<223> OTHER INFORMATION: synthetic primer

<400> SEQUENCE: 36
acatattccc gttatgcatc g                                          21

<210> SEQ ID NO 37
<211> LENGTH: 22
<212> TYPE: DNA
<213> ORGANISM: Artificial Sequence
<220> FEATURE:
<223> OTHER INFORMATION: synthetic primer

<400> SEQUENCE: 37
gcttgggctg caggtcgaga tc                                         22

<210> SEQ ID NO 38
<211> LENGTH: 26
<212> TYPE: DNA
<213> ORGANISM: Artificial Sequence
<220> FEATURE:
<223> OTHER INFORMATION: synthetic primer

<400> SEQUENCE: 38
gttcaaaatg gtatgcgttt tgacac                                     26

<210> SEQ ID NO 39
<211> LENGTH: 77
<212> TYPE: DNA
<213> ORGANISM: Artificial Sequence
<220> FEATURE:
<223> OTHER INFORMATION: synthetic primer

<400> SEQUENCE: 39
taaaaatttt acaaaaggt attgactttc cctacagggt gtgtaataat ttaattgacg  60
gtaaataaca aaagagg                                               77

<210> SEQ ID NO 40
<211> LENGTH: 51
<212> TYPE: DNA
<213> ORGANISM: Artificial Sequence
<220> FEATURE:
<223> OTHER INFORMATION: synthetic primer

<400> SEQUENCE: 40
caataccttt ttgtaaaatt tttagaaata aacttacaat ttgagaaaaa c          51

<210> SEQ ID NO 41
<211> LENGTH: 79
<212> TYPE: DNA
<213> ORGANISM: Artificial Sequence
<220> FEATURE:
<223> OTHER INFORMATION: synthetic primer

<400> SEQUENCE: 41
cagagtagac ttacttaaaa gactattctg caatctttat tcatttgtcc ttataattaa  60
attattacac accctgtag                                              79
```

<210> SEQ ID NO 42
<211> LENGTH: 53
<212> TYPE: DNA
<213> ORGANISM: Artificial Sequence
<220> FEATURE:
<223> OTHER INFORMATION: synthetic primer

<400> SEQUENCE: 42
ttttaagtaa gtctactctg aatttttta dacggtaaat aacaaaagag ggg    53

<210> SEQ ID NO 43
<211> LENGTH: 87
<212> TYPE: DNA
<213> ORGANISM: Artificial Sequence
<220> FEATURE:
<223> OTHER INFORMATION: synthetic primer

<400> SEQUENCE: 43
gtgtaaggag aaggacaggt gctgcccttc gataaaatca atctttattc atttgtcctt    60
ataattaaat tattacacac cctgtag    87

<210> SEQ ID NO 44
<211> LENGTH: 61
<212> TYPE: DNA
<213> ORGANISM: Artificial Sequence
<220> FEATURE:
<223> OTHER INFORMATION: synthetic primer

<400> SEQUENCE: 44
cctgtccttc tccttacact ttgagggagg tgaacacaga cggtaaataa caaagaggg    60 g    61

<210> SEQ ID NO 45
<211> LENGTH: 25
<212> TYPE: DNA
<213> ORGANISM: Artificial Sequence
<220> FEATURE:
<223> OTHER INFORMATION: synthetic primer

<400> SEQUENCE: 45
atacatcggc gagtttgata gagga    25

<210> SEQ ID NO 46
<211> LENGTH: 50
<212> TYPE: DNA
<213> ORGANISM: Artificial Sequence
<220> FEATURE:
<223> OTHER INFORMATION: synthetic primer

<400> SEQUENCE: 46
aacatggtag aacaaactaa agatccaaaa catcaccctt cgatccgaaa    50

<210> SEQ ID NO 47
<211> LENGTH: 50
<212> TYPE: DNA
<213> ORGANISM: Artificial Sequence
<220> FEATURE:
<223> OTHER INFORMATION: synthetic primer

<400> SEQUENCE: 47
agggaaaagg tggtgaacta ctgtggaaga gtattatatg aagctggcct    50

<210> SEQ ID NO 48
<211> LENGTH: 27

-continued

```
<212> TYPE: DNA
<213> ORGANISM: Artificial Sequence
<220> FEATURE:
<223> OTHER INFORMATION: synthetic primer

<400> SEQUENCE: 48
gatctttagt ttgttctacc atgtttt                                        27

<210> SEQ ID NO 49
<211> LENGTH: 23
<212> TYPE: DNA
<213> ORGANISM: Artificial Sequence
<220> FEATURE:
<223> OTHER INFORMATION: synthetic primer

<400> SEQUENCE: 49
cacagtagtt caccaccttt tcc                                            23

<210> SEQ ID NO 50
<211> LENGTH: 50
<212> TYPE: DNA
<213> ORGANISM: Artificial Sequence
<220> FEATURE:
<223> OTHER INFORMATION: synthetic primer

<400> SEQUENCE: 50
tgaaataaag gaggaattca aaatggaaga gtattatatg aagctggcct               50

<210> SEQ ID NO 51
<211> LENGTH: 24
<212> TYPE: DNA
<213> ORGANISM: Artificial Sequence
<220> FEATURE:
<223> OTHER INFORMATION: synthetic primer

<400> SEQUENCE: 51
cattttgaat tcctccttta tttc                                           24
```